United States Patent [19]
Storni

[11] Patent Number: 4,559,349
[45] Date of Patent: Dec. 17, 1985

[54] CARBOXAMIDES

[75] Inventor: Angelo Storni, Rheinfelden, Switzerland

[73] Assignee: Ciba Geigy Corporation, Ardsley, N.Y.

[21] Appl. No.: 586,493

[22] Filed: Mar. 5, 1984

[30] Foreign Application Priority Data

Mar. 9, 1983 [CH] Switzerland .................. 1258/83
Jul. 18, 1983 [CH] Switzerland .................. 3925/83

[51] Int. Cl.$^4$ .................................. A61K 31/445
[52] U.S. Cl. ............................ 514/318; 514/336; 514/357; 546/193; 546/194; 546/210; 546/212; 546/225; 546/233; 546/234
[58] Field of Search ............... 546/193, 194, 210, 212, 546/225, 233, 234

[56] References Cited

U.S. PATENT DOCUMENTS

| | | | |
|---|---|---|---|
| 3,197,473 | 7/1965 | Klosa | 546/194 |
| 3,632,767 | 1/1972 | Gray et al. | 546/225 |
| 3,956,296 | 5/1976 | Duncan, Jr. et al. | 546/194 |
| 4,335,127 | 6/1982 | Vandenberk et al. | 546/225 |

FOREIGN PATENT DOCUMENTS 13612 7/1980 European Pat. Off. .

Primary Examiner—Paul R. Michl
Assistant Examiner—Alex H. Walker
Attorney, Agent, or Firm—Michael W. Glynn

[57] ABSTRACT

The invention relates especially to pharmaceutical preparations containing N-(piperidinyl-alkyl)-carboxamides of the general formula

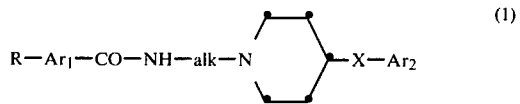

in which
R represents hydroxy, hydroxy etherified by an aliphatic alcohol, or halogen,
$Ar_1$ represents a monocyclic arylene or heteroarylene radical,
alk represents an alkylene group that separates the two N atoms by at least two carbon atoms,
X represents a free or ketalized carbonyl group, free hydroxymethylene or hydroxymethylene esterified by an organic carboxylic acid, or methylene, and
$Ar_2$ represents a monocyclic aryl or heteroaryl radical, and salts thereof, the use of these compounds of the formula I and salts thereof, novel compounds of the formula I and salts thereof in which R, $Ar_1$, alk, X and $Ar_2$ have the meanings given, with the proviso that the grouping R—$Ar_1$ is other than a radical of the formula

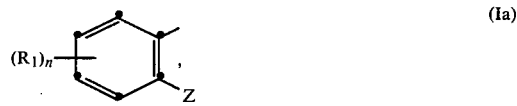

in which $R_1$ is selected from the group consisting of lower alkyl, trifluoromethyl, halogen, lower alkoxy, nitro and cyano and at least one of the radicals $R_1$ represents halogen or lower alkoxy, n represents an integer from 1 to 3, and Z represents nitro, amino, lower alkylamino, arylamino, aryl-lower alkylamino, (thio-)formylamino, (thio-)lower alkanoylamino, (thio-)aroylamino or aryl-(thio-)lower alkanoylamino, if alk and X have the meanings given and $Ar_2$ represents unsubstituted phenyl, thienyl or pyridyl or substituted phenyl having one, two or three substituents selected from the group consisting of halogen, lower alkyl, lower alkoxy, trifluoromethyl and amino, and to processes for the manufacture thereof.

17 Claims, No Drawings

CARBOXAMIDES

The invention relates to pharmaceutical preparations containing carboxamides, especially N-(piperidinyl-alkyl)-carboxamides and salts thereof, processes for the manufacture thereof, the use of these compounds, novel N-(piperidinyl-alkyl)-carboxamides and processes for the manufacture thereof.

The invention relates especially to pharmaceutical preparations containing N-(piperidinyl-alkyl)-carboxamides of the general formula

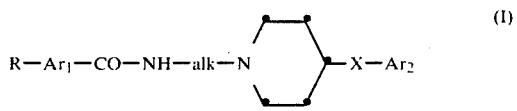

in which
R represents hydroxy, hydroxy esterified by an aliphatic alcohol, or halogen,
$Ar_1$ represents a monocyclic arylene or heteroarylene radical,
alk represents an alkylene group that separates the two N atoms by at least two carbon atoms,
X represents a free or ketalised carbonyl group, free hydroxymethylene or hydroxymethylene esterified by an organic carboxylic acid, or methylene, and
$Ar_2$ represents a monocyclic aryl or heteroaryl radical, and salts thereof, the use of these compounds of the formula I and salts thereof, novel compounds of the formula I and salts thereof in which R, $Ar_1$, alk, X and $Ar_2$ have the meanings given, with the proviso that the grouping R—$Ar_1$ is other than a radical of the formula

in which $R_1$ is selected from the group consisting of lower alkyl, trifluoromethyl, halogen, lower alkoxy, nitro and cyano and at least one of the radicals $R_1$ represents halogen or lower alkoxy, n represents an integer from 1 to 3, and Z represents nitro, amino, lower alkylamino, arylamino, aryl-lower alkylamino, (thio-)formylamino, (thio-)lower alkanoylamino, (thio-)aroylamino or aryl-(thio-)lower alkanoylamino, if alk and X have the meanings given and $Ar_2$ represents unsubstituted phenyl, thienyl or pyridyl or substituted phenyl having one, two or three substituents selected from the group consisting of halogen, lower alkyl, lower alkoxy, trifluoromethyl and amino, and to processes for the manufacture thereof.

A monocyclic arylene radical $Ar_1$ is especially unsubstituted or mono- or poly-substituted phenylene, especially 1,2-phenylene, and also 1,3- or 1,4-phenylene.

A monocyclic heteroarylene radical $Ar_1$ is, for example, monocyclic azaarylene having up to and including 3 nitrogen atoms and bonded by a carbon atom, especially unsubstituted or mono- or poly-substituted pyridylene, especially pyridylene in which the carbamoyl group is bonded in position 3 and the radical R in position 2 of the pyridylene ring, such as 2,3-pyridylene, also 3,2-, 2,4-, 2,5-, 2,6-, 3,4- or 3,5-pyridylene. In the phenylene or pyridylene ring the carbamoyl group is preferably bonded to a carbon atom adjacent to the radical R.

As substituents of the above-mentioned arylene or heteroarylene radicals, in addition to the radical R and the CO-grouping, there come into consideration, for example, aliphatic radicals, hydroxy, hydroxy esterified by an organic carboxylic acid or by an inorganic acid or hydroxy etherified by an aliphatic alcohol, acyl, nitro, carboxy, for example carboxy esterified by an aliphatic alcohol, cyano, unsubstituted carbamoyl or carbamoyl mono- or di-substituted, for example, by an aliphatic radical, unsubstituted amino or amino mono- or di-substituted, for example, by an aliphatic radical, unsubstituted sulphamoyl or sulphamoyl mono- or di-substituted, for example, by an aliphatic radical, or mercapto substituted, for example, by an aliphatic radical, and/or sulphinyl or sulphonyl each substituted, for example, by an aliphatic radical.

Aliphatic radicals are especially in each case lower alkyl, also, for example, lower alkenyl or lower alkadienyl, or halo-lower alkyl. Hydroxy esterified by an organic carboxylic acid is, in this context, especially lower alkanoyloxy, and hydroxy esterified by an inorganic acid is especially halogen, whilst hydroxy etherified by an aliphatic alcohol is especially lower alkoxy, and also, for example, lower alkenyloxy, or halo-lower alkoxy.

Acyl is derived especially from an organic carboxylic acid and is more especially lower alkanoyl. Carboxy esterified by an aliphatic alcohol is especially lower alkoxycarbonyl. In carbamoyl or amino or sulphamoyl that is mono- or di-substituted by an aliphatic radical, the group in question is mono- or di-substituted especially by lower alkyl. Such radicals are, for example, N-lower alkylcarbamoyl or N,N-di-lower alkylcarbamoyl, N-lower alkylamino or N,N-di-lower alkylamino, or N-lower alkylsulphamoyl or N,N-di-lower alkylsulphamoyl. Mercapto substituted by an aliphatic radical is especially lower alkylthio or halo-lower alkylthio, whilst there is to be understood by sulphinyl or sulphonyl each substituted by an aliphatic radical especially lower alkane- or halo-lower alkane-sulphinyl or -sulphonyl.

An alkylene group alk that separates the two N atoms by at least two carbon atoms is especially corresponding alkylene separating the two N atoms by 2 or 3 carbon atoms, for example alkylene having from 2 up to and including 7, especially 2 or 3, carbon atoms.

A ketalised carbonyl group X is ketalised, for example, by a mono- or di-hydric aliphatic alcohol and is especially di-lower alkoxymethylene or lower alkylenedioxymethylene.

Hydroxymethylene X that is esterified by an organic carboxylic acid is especially lower alkanoyloxymethylene.

A monocyclic aryl radical $Ar_2$ is especially an unsubstituted or a mono- or poly-substituted phenyl radical, whilst a monocyclic heteroaryl radical $Ar_2$ is, for example, a monocyclic monooxa-, monoaza- or monothiaaryl radical, especially unsubstituted or mono- or poly-substituted furyl, pyridyl or thienyl.

As substituents of aryl or heteroaryl radicals $Ar_2$ there come into consideration, for example, those mentioned for $Ar_1$, especially halogen, and also lower alkoxy.

Unless defined to the contrary, the general definitions used hereinbefore and hereinafter have especially the following meanings.

The term "lower" denotes that the correspondingly designated organic groups or compounds contain preferably up to and including 7, and especially up to and including 4, carbon atoms.

Halogen is especially halogen having an atomic number of up to and including 35, such as fluorine, chlorine or bromine, and also includes iodine.

Lower alkoxy is, for example, methoxy, ethoxy, n-propoxy, isopropoxy, n-butoxy, isobutoxy, sec.-butoxy, tert.-butoxy, and includes also corresponding pentyloxy, hexyloxy and heptyloxy radicals.

Lower alkenyloxy is, for example, allyloxy or but-2-enyloxy or but-3-enyloxy.

Lower alkyl is, for example, methyl, ethyl, n-propyl, isopropyl, n-butyl, isobutyl, sec.-butyl, tert.-butyl, and includes also corresponding pentyl, hexyl and heptyl radicals.

Lower alkenyl is, for example, 2-propenyl or 1-, 2- or 3-butenyl, and lower alkadienyl is, for example, butadien-1,3-yl.

Halo-lower alkyl is, for example, trifluoromethyl, 1,1,2-trifluoro-2-chloroethyl or chloromethyl.

Lower alkanoyloxy is, for example, acetoxy, propionyloxy, butyryloxy, isobutyryloxy or pivaloyloxy.

Halo-lower alkoxy is, for example, difluoromethoxy or 1,1,2-trifluoro-2-chloroethoxy.

Lower alkanoyl is, for example, formyl, acetyl, propionyl, butyryl, isobutyryl or pivaloyl.

Lower alkoxycarbonyl is, for example, methoxy-, ethoxy-, propoxy- or pivalyloxy-carbonyl.

N-lower alkylcarbamoyl is, for example, N-methyl-, N-ethyl-, N-(n-propyl)- or N-isopropyl-carbamoyl, whilst N,N-di-lower alkylcarbamoyl is, for example, N,N-dimethyl-or N,N-diethyl-carbamoyl.

N-lower alkylamino is, for example, N-methyl-, N-ethyl-, N-(n-propyl)- or N-isopropyl-amino, whilst N,N-di-lower alkylamino is, for example, N,N-dimethyl-or N,N-diethyl-amino.

N-lower alkylsulphamoyl is, for example, N-methyl- or N-ethyl-sulphamoyl, and N,N-di-lower alkylsulphamoyl is, for example, N,N-dimethyl- or N,N-diethyl-sulphamoyl.

Lower alkylthio is, for example, methyl-, ethyl-, n-propyl-, isopropyl-, n-butyl-, isobutyl-, sec.-butyl-or tert.-butyl-thio.

Halo-lower alkylthio is, for example, chloromethyl-, trifluoromethyl- or 1,1,2-trifluoro-2-chloroethyl-thio.

Lower alkane-sulphinyl or -sulphonyl is, for example, methane-, ethane-, n-propane- or isopropane-sulphinyl or -sulphonyl.

Halo-lower alkane-sulphinyl or -sulphonyl is, for example, chloromethane-, trifluoromethane- or 1,1,2-trifluoro-2-chloroethane-sulphinyl or -sulphonyl.

2- or 3-membered alkylene having from 2 to 7, especially 2 or 3, carbon atoms is, for example, ethylene or 1,3-propylene, also 1,2-propylene and 2-methyl-1,2-propylene.

Lower alkylenedioxy is, for example, ethylenedioxy or 1,3-propylenedioxy.

Thienyl is, for example, 2-thienyl, also 3-thienyl, and furyl is, for example, 2-furyl, also 3-furyl, whilst pyridyl is, for example, 2- or 3-pyridyl and also 4-pyridyl.

Salts of compounds of the formula (I) are preferably pharmaceutically acceptable salts. Owing to their basic group(s), compounds of the formula (I) may form, for example, acid addition salts. These are formed, for example, with strong inorganic acids, such as mineral acids, for example sulphuric acid, phosphoric acids or hydrohalic acids, or with strong organic acids, such as lower alkanecarboxylic acids, for example acetic acid, optionally unsaturated dicarboxylic acids, for example oxalic, malonic, maleic or fumaric acid, hydroxycarboxylic acids, for example tartaric acid or citric acid, or arylcarboxylic acids, for example benzoic acid. Also suitable for the formation of acid addition salts are, for example, sulphonic acids, such as lower alkanesulphonic acids, for example methanesulphonic acid, or optionally substituted benzenesulphonic acids, for example p-toluenesulphonic acid. The invention relates also to salts that are unsuitable for pharmaceutical uses, since these may be used, for example, for the isolation or purification of corresponding free compounds of the formula (I) and their pharmaceutically acceptable salts.

The compounds according to the invention may be in the form of structural isomers. For example, if compounds of the formula (I) have chiral carbon atoms, for example if X in the formula (I) represents free hydroxymethylene or hydroxymethylene esterified by an organic carboxylic acid, they may, for example, be in the form of pure enantiomers or mixtures of enantiomers, such as racemates, and if, in addition, at least one further chiral centre is present, in the form of diastereoisomers or mixtures of diastereoisomers.

The compounds of the formula (I) and their pharmaceutically acceptable salts may be used, for example, as medicaments, for example as antipsychotic agents, or in a method for the prophylactic or therapeutic treatment of the human and also the animal body. Thus, the compounds of the formula (I) exhibit, in particular, valuable pharmacological properties. They possess, above all, a pronounced anti-psychotic action. For example, as investigations analogous to those of B. Costall et al., Brain Research 123, 89–111 (1977) have shown, the compounds of the formula (I) antagonise the amphetamine-induced stereotyping of rats at a dosage of from approximately 1 mg/kg in the case of intraperitoneal administration.

As demonstrated by investigations on rats in accordance with the test procedure of P. C. Waldmeier, Experientia 36, 1092–4 (1980), with intraperitoneal administration of the active ingredients in a dosage range of from approximately 0.1 to approximately 100 mg/kg, the compounds of the formula (I) possess a pronounced antidopaminergic activity. This is determined by the rate of formation of metabolites of the neuro-transmitter dopamine (DA) since the increase in the DA conversion may be regarded as a measure of the dopamine-receptor blockade.

The DA-receptor blockade by compounds of the formula (I) can also be detected directly by the in vivo inhibition of the [$^3$H] spiperone bond in the hippocampus region of rats. In the radioreceptor assay in accordance with S. Bischoff et al., European J. Pharmacol., 68, 305–315 (1980), a strong dopamine-receptor blockade action was demonstrated in a dosage range of from approximately 0.01 to approximately 100 mg/kg after intraperitoneal administration to rats.

Accordingly, for example owing to their strong antidopaminergic activity, the compounds of the formula (I) and their salts may be used, for example, as antipsychotic agents, especially having effect on the hippocampal dopaminergic system. Especially advantageous is the fact that, when using compounds of the formula (I), only slight or no extrapyramidal side effects are to be observed.

In the use of compounds of the formula I, there can be included, in addition to the propylacetic and/or therapeutic administration, also the commercial processing of the active substance.

The invention relates especially to pharmaceutical preparations containing compounds of the formula (I) in which R represents hydroxy, lower alkoxy, lower alkenyloxy or halogen, $Ar_1$ represents a phenylene radical or a monocyclic azaarylene radical having up to and including 3 nitrogen atoms and bonded by a carbon atom, each of which radicals is unsubstituted or mono- or poly-substituted by lower alkyl, lower alkenyl, lower alkadienyl, halo-lower alkyl, hydroxy, lower alkanoyloxy, halogen, lower alkoxy, lower alkenyloxy, halo-lower alkoxy, lower alkanoyl, nitro, cyano, carbamoyl, N-lower alkylcarbamoyl, N,N-di-lower alkylcarbamoyl, carboxy, lower alkoxycarbonyl, amino, N-lower alkylamino, N,N-di-lower alkylamino, sulphamoyl, N-lower alkylsulphamoyl, N,N-di-lower alkylsulphamoyl, lower alkylthio, halo-lower alkylthio, lower alkanesulphinyl, halo-lower alkanesulphinyl, lower alkanesulphonyl and/or by halo-lower alkanesulphonyl, alk represents alkylene that has from 2 up to and including 7 carbon atoms and separates the two N atoms by 2 or 3 carbon atoms, X represents carbonyl, di-lower alkoxymethylene, lower alkylenedioxymethylene, hydroxymethylene, lower alkanoyloxymethylene or methylene and $Ar_2$ represents a phenyl radical or a monocyclic monooxa-, monoaza- or monothia-aryl radical, each of which radicals is unsubstituted or mono- or poly-substituted by lower alkyl, lower alkenyl, lower alkadienyl, halo-lower alkyl, hydroxy, lower alkanoyloxy, halogen, lower alkoxy, lower alkenyloxy, halo-lower alkoxy, lower alkanoyl, nitro, cyano, carbamoyl, N-lower alkylcarbamoyl, N,N-di-lower alkylcarbamoyl, carboxy, lower alkoxycarbonyl, amino, N-lower alkylamino, N,N-di-lower alkylamino, sulphamoyl, N-lower alkylsulphamoyl, N,N-di-lower alkylsulphamoyl, lower alkylthio, halo-lower alkylthio, lower alkane-sulphinyl, halo-lower alkanesulphinyl, lower alkane-sulphonyl and/or by halo-lower alkanesulphonyl, and salts thereof, the use of these compounds of the formula (I) and salts thereof, novel compounds of the formula (I) and salts thereof in which R, $Ar_1$, alk, X and $Ar_2$ have the meanings given, with the proviso that the grouping R—$Ar_1$ is other than a radical of the formula (Ia) in which $R_1$ is selected from the group consisting of lower alkyl, trifluoromethyl, halogen, lower alkoxy, nitro and cyano and at least one of the radicals $R_1$ represents halogen or lower alkoxy, n represents an integer from 1 to 3, and Z represents nitro, amino or lower alkylamino, if alk and X have the meanings given and $Ar_2$ represents unsubstituted phenyl, thienyl or pyridyl or substituted phenyl having one, two or three substituents selected from the group consisting of lower alkyl, trifluoromethyl, halogen, lower alkoxy and amino, and to processes for the manufacture thereof.

The invention relates especially to pharmaceutical preparations containing compounds of the formula (I) in which R represents hydroxy, lower alkoxy, lower alkenyloxy or halogen, $Ar_1$ represents phenylene or pyridylene each of which is unsubstituted or mono- or poly-substituted by lower alkyl, lower alkenyl, lower alkadienyl, halo-lower alkyl, hydroxy, lower alkanoyloxy, halogen, lower alkoxy, lower alkenyloxy, halo-lower alkoxy, lower alkanoyl, nitro, cyano, carbamoyl, N-lower alkylcarbamoyl, N,N-di-lower alkylcarbamoyl, amino, N-lower alkylamino, N,N-di-lower alkylamino, sulphamoyl, N-lower alkylsulphamoyl, N,N-di-lower alkylsulphamoyl, lower alkylthio, halo-lower alkylthio, lower alkanesulphinyl, halo-lower alkanesulphinyl, lower alkanesulphonyl and/or by halo-lower alkanesulphonyl, alk represents alkylene that has from 2 up to and including 7 carbon atoms and separates the two N atoms by 2 or 3 carbon atoms, X represents carbonyl, di-lower alkoxymethylene, lower alkylenedioxymethylene, hydroxymethylene, lower alkanoyloxymethylene or methylene and $Ar_2$ represents a phenyl, thienyl, furyl or pyridyl radical each of which is unsubstituted or mono- or poly-substituted by lower alkyl, lower alkenyl, halo-lower alkyl, hydroxy, lower alkanoyloxy, halogen, lower alkoxy, lower alkenyloxy, halo-lower alkoxy, lower alkanoyl, nitro, cyano, carbamoyl, N-lower alkylcarbamoyl, N,N-di-lower alkylcarbamoyl, amino, N-lower alkylamino, N,N-di-lower alkylamino, sulphamoyl, N-lower alkylsulphamoyl, N,N-di-lower alkylsulphamoyl, lower alkylthio, halo-lower alkylthio, lower alkanesulphinyl, halo-lower alkanesulphinyl, lower alkanesulphonyl and/or by halo-lower alkanesulphonyl, and salts thereof, the use of these compounds of the formula (I) and salts thereof, novel compounds of the formula (I) and salts thereof in which R, $Ar_1$, alk, X and $Ar_2$ have the meanings given, with the proviso that the grouping R—$Ar_1$ is other than a radical of the formula (Ia) in which $R_1$ is selected from the group consisting of lower alkyl, trifluoromethyl, halogen, lower alkoxy, nitro and cyano and at least one of the radicals $R_1$ represents halogen or lower alkoxy, n represents an integer from 1 to 3, and Z represents nitro, amino or lower alkylamino, if alk and X have the meanings given and $Ar_2$ represents unsubstituted phenyl, thienyl or pyridyl or substituted phenyl having one, two or three substituents selected from the group consisting of lower alkyl, trifluoromethyl, halogen, lower alkoxy and amino, and to processes for the manufacture thereof.

The invention relates especially to pharmaceutical preparations containing compounds of the formula (I) in which R represents lower alkoxy, for example having up to and including 4 carbon atoms, such as methoxy, $Ar_1$ represents phenylene, for example 1,2-phenylene, or pyridylene, for example 3,2-pyridylene, each of which is unsubstituted or mono- or poly-substituted by lower alkyl, for example having up to and including 4 carbon atoms, such as methyl, halo-lower alkyl, for example having up to and including 4 carbon atoms, such as trifluoromethyl, halogen, for example having an atomic number of up to and including 35, such as fluorine, chlorine or bromine, lower alkoxy, for example having up to and including 4 carbon atoms, such as methoxy, cyano, carbamoyl, amino, N-lower alkylamino, for example having up to and including 4 carbon atoms, such as N-methylamino, N,N-di-lower alkylamino, for example having up to and including 4 carbon atoms in each lower alkyl moiety, such as N,N-dimethylamino, sulphamoyl, N,N-di-lower alkylsulphamoyl, for example having up to and including 4 carbon atoms in each alkyl moiety, such as N,N-dimethylsulphamoyl, halo-lower alkylthio, for example having up to and including 4 carbon atoms, such as trifluoromethylthio, lower alkanesulphonyl, for example having up to and including 4 carbon atoms, such as methanesulphonyl, and/or by halo-lower alkanesulphonyl, for example having up to and including 4 carbon atoms, such as trifluoromethanesulphonyl, alk represents alkylene that has 2 or 3 carbon atoms and separates the two N atoms by 2 or 3 carbon atoms, such as ethylene or 1,3-propylene, X represents carbonyl, hydroxymethylene or methylene and $Ar_2$ represents phenyl substituted by halogen, for example having an atomic number of up to and including 35, such as fluorine, or unsubstituted thienyl, and salts thereof, the use of these compounds of the formula (I) and salts thereof, novel compounds of the formula (I) and salts thereof in which R, $Ar_1$, alk, X and $Ar_2$ have the meanings given, with the proviso that the grouping R—$Ar_1$ is other than a radical of the formula (Ia) in which $R_1$ is selected from the group consisting of lower alkyl, trifluoromethyl, halogen, lower alkoxy and cyano and at least one of the radicals $R_1$ represents halogen or lower alkoxy, n represents an integer from 1 up to and including 3, and Z represents amino or lower alkylamino, if alk and X have the meanings given and $Ar_2$ represents unsubstituted thienyl or phenyl substituted once, twice or three times by halogen, and to processes for the manufacture thereof.

The invention relates especially to pharmaceutical preparations containing compounds of the formula (I) in which, on the one hand, R represents lower alkoxy, especially having up to and including 4 carbon atoms, such as methoxy, or halogen, especially having an atomic number of up to and including 35, such as fluorine, and $Ar_1$ represents phenylene which is unsubstituted or mono- or poly-substituted by lower alkyl, especially having up to and including 4 carbon atoms, such as methyl, halo-lower alkyl, especially having an atomic number of up to and including 35 and having up to and including 4 carbon atoms, such as trifluoromethyl, hydroxy, halogen, especially having an atomic number of up to and including 35, such as bromine, lower alkoxy, especially having up to and including 4 carbon atoms, such as methoxy, cyano, carbamoyl, lower alkoxycarbonyl, especially having from 2 up to and including 5 carbon atoms, such as methoxycarbonyl, amino, lower alkylamino, especially having up to and including 4 carbon atoms, such as methylamino, di-lower alkylamino, especially having up to and including 4 carbon atoms in each lower alkyl moiety, such as dimethylamino, sulphamoyl, N,N-di-lower alkylsulphamoyl, especially having up to and including 4 carbon atoms in each lower alkyl moiety, such as N,N-dimethylsulphamoyl, lower alkylthio, especially having up to and including 4 carbon atoms, such as methylthio, lower alkanesulphinyl, especially having up to and including 4 carbon atoms, such as methanesulphinyl, and/or by lower alkanesulphonyl, especially having up to and including 4 carbon atoms, such as methanesulphonyl, or in which, on the other hand, R represents lower alkoxy, especially having up to and including 4 carbon atoms, such as methoxy, and $Ar_1$ represents pyridylene, especially 3,2-pyridylene, which is unsubstituted or substituted by lower alkoxy, especially having up to and including 4 carbon atoms, such as methoxy, and in each case alk represents alkylene that has from 2 up to and including 7 carbon atoms and separates the two N atoms by 2 or 3 carbon atoms, X represents carbonyl, hydroxymethylene or methylene and $Ar_2$ represents phenyl substituted by halogen, especially having an atomic number of up to and including 35, such as fluorine, or unsubstituted thienyl, and salts thereof, the use of these compounds of the formula (I) and salts thereof, novel compounds of the formula (I) and salts therof in which R, $Ar_1$, alk, X and $Ar_2$ have the meanings given, with the proviso that the grouping R—$Ar_1$ is other than a radical of the formula (Ia) in which $R_1$ is selected from the group consisting of lower alkyl, trifluoromethyl, halogen, lower alkoxy and cyano and at least one of the radicals $R_1$ represents halogen or lower alkoxy, n represents an integer from 1 up to and including 3, and Z represents amino or lower alkylamino, if alk and X have the meanings given and $Ar_2$ represents unsubstituted thienyl or phenyl substituted once, twice or three times by halogen, and to processes for the manufacture thereof.

The invention relates more especially to pharmaceutical preparations containing compounds of the formula (I) in which R in each case represents lower alkoxy, for example having up to and including 4 carbon atoms, such as methoxy, $Ar_1$ represents, on the one hand, a phenyl radical which is unsubstituted or mono- or poly-substituted by halo-lower alkyl, for example having up to and including 4 carbon atoms, such as trifluoromethyl, halogen, for example having an atomic number of up to and including 35, such as fluorine, chlorine or bromine, lower alkoxy, for example having up to and including 4 carbon atoms, such as methoxy, cyano, carbamoyl, N-lower alkylamino, for example having up to and including 4 carbon atoms, such as methylamino, sulphamoyl, N,N-di-lower alkylsulphamoyl, for example having up to and including 4 carbon atoms, such as dimethylsulphamoyl, halo-lower alkylthio, for example having up to and including 4 carbon atoms, such as trifluoromethylthio, and/or by halo-lower alkanesulphonyl, for example having up to and including 4 carbon atoms, such as trifluoromethanesulphonyl, or, on the other hand, a pyridylene radical, such as 3,2-pyridylene, which is mono- or poly-substituted by lower alkoxy, for example having up to and including 4 carbon atoms, such as methoxy, and/or by halogen, for example having an atomic number of up to and including 35, such as chlorine, alk represents ethylene or 1,3-propylene, X represents carbonyl, hydroxymethylene or methylene and $Ar_2$ represents a phenyl radical substituted by halogen, for example having an atomic number of up to and including 35, such as fluorine, and salts thereof, the use of these compounds and salts thereof, novel compounds of the formula (I) and salts thereof in which R, $Ar_1$, alk, X and $Ar_2$ have the meanings given, with the proviso that the grouping R—$Ar_1$ is other than a radical of the formula (Ia) in which $R_1$ is selected from the group consisting of trifluoromethyl, halogen, lower alkoxy and cyano and at least one of the radicals $R_1$ represents halogen or lower alkoxy, n represents an integer from 1 up to and including 3, and Z represents lower alkylamino, if alk and X have the meanings given and $Ar_2$ represents phenyl substituted once, twice or three times by halogen, and to processes for the manufacture thereof.

The invention relates more especially to pharmaceutical preparations containing compounds of the formula (I) in which the grouping R—$Ar_1$ represents the structural element of the formula

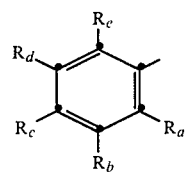

(Ib)

in which one of the radicals $R_a$ and $R_c$ represents the radical R which represents lower alkoxy, especially having up to and including 4 carbon atoms, such as methoxy, or halogen, especially having an atomic number of up to and including 35, such as fluorine, and the other represents hydrogen, lower alkyl, especially having up to and including 4 carbon atoms, such as methyl, halogen, especially having an atomic number of up to and including 35, such as bromine, or lower alkylamino, especially having up to and including 4 carbon atoms, such as methylamino, and each of the radicals $R_b$, $R_d$ and $R_e$, independently of the others, represents hydrogen, lower alkyl, especially having up to and including 4 carbon atoms, such as methyl, halo-lower alkyl, especially having an atomic number of up to and including 35 and having up to and including 4 carbon atoms, such as trifluoromethyl, hydroxy, halogen, especially having an atomic number of up to and including 35, such as chlorine, lower alkoxy, especially having up to and including 4 carbon atoms, such as methoxy, cyano, carbamoyl, lower alkoxycarbonyl, especially having from 2 up to and including 5 carbon atoms, such as methoxycarbonyl, amino, sulphamoyl, N,N-di-lower alkylsulphamoyl, especially having up to and including 4 carbon atoms in each alkyl moiety, such as dimethylsulphamoyl, lower alkylthio, especially having up to and including 4 carbon atoms, such as methylthio, lower alkanesulphinyl, especially having up to and including 4 carbon atoms, such as methanesulphinyl, and/or lower alkanesulphonyl, especially having up to and including 4 carbon atoms, such as methanesulphonyl, and in which alk represents alkylene that has from 2 up to and including 4 carbon atoms and separates the two N atoms by 2 or 3 carbon atoms, X represents carbonyl, hydroxymethylene or methylene and $Ar_2$ represents phenyl substituted by halogen, especially having an atomic number of up to and including 35, such as fluorine, or unsubstituted thienyl, and salts thereof, the use of these compounds and salts thereof, novel compounds of the formula (I) and salts thereof in which R, $Ar_1$, alk, X and $Ar_2$ have the meanings given, with the proviso that the grouping R—$Ar_1$ is other than a radical of the formula (IB) in which $R_a$ or $R_e$ represents amino or lower alkylamino and one, two or three of the remaining radicals $R_a$, $R_b$, $R_c$, $R_d$ and $R_e$ is (are) selected from the group consisting of lower alkyl, trifluoromethyl, halogen, lower alkoxy and cyano and the others represent hydrogen, at least one of these radicals representing halogen or lower alkoxy, if alk and X have the meanings given and $Ar_2$ represents unsubstituted thienyl, or phenyl substituted once, twice or three times by halogen, and to processes for the manufacture thereof.

The invention relates more especially to pharmaceutical preparations containing compounds of the formula (I) in which the grouping R—$Ar_1$ represents the structural element of the formula Ib in which, on the one hand, the radical $R_a$ represents the radical R which represents lower alkoxy having up to and including 4 carbon atoms, such as methoxy, and $R_c$ represents hydrogen, halogen having an atomic number of up to and including 35, such as fluorine, or lower alkylamino having up to and including 4 carbon atoms, such as methylamino, or $R_a$ represents hydrogen and $R_c$ represents the radical R which represents lower alkoxy having up to and including 4 carbon atoms, or in which, on the other hand, the radical $R_c$ represents the radical R which represents halogen having an atomic number of up to and including 35, such as fluorine, and $R_a$ represents hydrogen or halogen having an atomic number of up to and including 35, such as bromine, and one of the radicals $R_b$ and $R_d$ represents hydrogen, lower alkyl having up to and including 4 carbon atoms, such as methyl, halo-lower alkyl having an atomic number of up to and including 35 and having up to and including 4 carbon atoms, such as trifluoromethyl, halogen having an atomic number of up to and including 35, such as bromine, lower alkoxy having up to and including 4 carbon atoms, such as methoxy, cyano, carbamoyl, lower alkoxycarbonyl having from 2 up to and including 5 carbon atoms, such as methoxycarbonyl, lower alkylthio having up to and including 4 carbon atoms, such as methylthio, lower alkanesulphinyl having up to and including 4 carbon atoms, such as methanesulphinyl, or lower alkanesulphonyl having up to and including 4 carbon atoms, such as methanesulphonyl, and the other and $R_e$ represent hydrogen, and in which in each case alk represents alkylene that has from 2 up to and including 4 carbon atoms and separates the two N atoms by 2 or 3 carbon atoms, such as ethylene, X represents carbonyl or hydroxymethylene and $Ar_2$ represents phenyl substituted in the p-position by halogen having an atomic number of up to and including 35, such as fluorine, and salts thereof, the use of these compounds and salts thereof, novel compounds of the formula (I) and salts thereof in which R, $Ar_1$, alk, X and $Ar_2$ have the meanings given, and to processes for the manufacture thereof.

The invention relates more especially to pharmaceutical preparations containing compounds of the formula (I) in which $Ar_1$ represents, on the one hand, phenylene, such as 1,2-phenylene, which is mono- or poly-substituted by halogen having an atomic number of up to and including 35, such as chlorine, cyano and/or by N-lower alkylamino having up to and including 4 carbon atoms in the lower alkyl moiety, such as methylamino, or, on the other hand, pyridylene, such as 3,2-pyridylene, and in each case R represents lower alkoxy having up to and including 4 carbon atoms, such as methoxy, alk represents ethylene, X represents carbonyl and $Ar_2$ represents phenyl substituted by halogen having an atomic number of up to and including 35, such as fluorine, and salts thereof, the use of these compounds of the formula (I) and salts thereof, novel compounds of the formula I and salts thereof in which R, $Ar_1$, alk, X and $Ar_2$ have the meanings given, with the proviso that the grouping R—$Ar_1$ is other than a radical of the formula (Ia) in which $R_1$ is selected from the group consisting of halogen having an atomic number of up to and including 35 and lower alkoxy having up to and including 4 carbon atoms, n represents an integer from 1 up to and including 3, and Z represents lower alkylamino having up to and including 4 carbon atoms, and to processes for the manufacture thereof.

The invention relates most especially to pharmaceutical preparations containing compounds of the formula (I) in which R represents lower alkoxy having up to and including 4 carbon atoms, such as methoxy, $Ar_1$ represents 1,2-phenylene which is substituted, especially in the p-position to R, by cyano, alk represents ethylene, X represents carbonyl and $Ar_2$ represents phenyl which is substituted, especially in the p-position, by halogen having an atomic number of up to and including 35, such as fluorine, and salts thereof, the use of these compounds and salts thereof, novel compounds of the formula (I) and salts thereof in which R, $Ar_1$, alk, X and $Ar_2$ have the meanings given, and to processes for the manufacture thereof.

The invention relates most especially to pharmaceutical preparations containing compounds of the formula (I) in which the grouping R—Ar$_1$ represents the structural element of the formula (Ib) in which, on the one hand, R$_a$ represents the radical R which represents lower alkoxy having up to and including 4 carbon atoms, such as methoxy, R$_b$ and R$_c$ represent hydrogen, R$_e$ represents lower alkylamino having up to and including 4 carbon atoms, such as methylamino, and R$_d$ represents halogen having an atomic number of up to and including 35, such as chlorine, or R$_e$ represents hydrogen or halogen having an atomic number of up to and including 35, such as chlorine, and R$_d$ represents cyano, or in which, on the other hand, R$_a$, R$_d$ and R$_e$ represent hydrogen, R$_b$ represents halogen having an atomic number of up to and including 35, such as bromine, and R$_c$ represents the radical R which represents lower alkoxy having up to and including 4 carbon atoms, such as methoxy, and in each case alk represents ethylene, X represents carbonyl or also hydroxymethylene and Ar$_2$ represent 4-fluorophenyl, and salts thereof, the use of these compounds and salts thereof, novel compounds of the formula (I) and salts thereof in which R, Ar$_1$, alk, X and Ar$_2$ have the meanings given, and to processes for the manufacture thereof.

The invention relates most especially to pharmaceutical preparations containing compounds of the formula (I) in which the grouping R—Ar$_1$ represents the structural element of the formula Ib in which one of the radicals R$_a$ and R$_b$ represents hydrogen or halogen having an atomic number of up to and including 35, such as bromine, and the other represents hydrogen, R$_c$ represents the radical R which represents halogen having an atomic number of up to and including 35, such as fluorine, and each of R$_d$ and R$_e$ represents hydrogen, and alk represents ethylene, X represents carbonyl and Ar$_2$ represents p-fluorophenyl, and salts thereof, the use of these compounds and salts thereof, novel compounds of the formula (I) and salts thereof in which R, Ar$_1$, alk, X and Ar$_2$ have the meanings given, and to processes for the manufacture thereof.

The invention relates first and foremost to pharmaceutical preparations containing compounds of the formula I in which the grouping R—Ar$_1$ represents the structural element of the formula Ib in which R$_a$, R$_d$ and R$_e$ represent hydrogen, R$_b$ represents hydrogen or halogen having an atomic number of up to and including 35, such as bromine, and R$_c$ represents the radical R which represents halogen having an atomic number of up to and including 35, such as fluorine, alk represents ethylene, X represents carbonyl and Ar$_2$ represents 4-fluorophenyl, and salts thereof, the use of these compounds and salts thereof, novel compounds of the formula (I) and salts thereof in which R, Ar$_1$, alk, X and Ar$_2$ have the meanings given, and to processes for the manufacture thereof.

The invention relates first and foremost to pharmaceutical preparations containing compounds of the formula I in which the grouping R—Ar$_1$ represents the structural element of the formula Ib in which R$_a$ represents the radical R which represents lower alkoxy having up to and including 4 carbon atoms, such as methoxy, R$_b$, R$_c$ and R$_e$ represent hydrogen, and R$_d$ represents cyano, alk represents ethylene, X represents carbonyl and Ar$_2$ represents 4-fluorophenyl, and salts thereof, the use of these compounds and salts thereof, novel compounds of the formula (I) and salts thereof in which R, Ar$_1$, alk, X and Ar$_2$ have the meanings given, and to processes for the manufacture thereof.

The invention relates especially to the compounds mentioned in the Examples, and the salts and isomers thereof.

The compounds of the formula (I) and salts thereof are manufactured according to methods known per se, for example as follows:

(a) a compound of the formula

in which X$_1$ represents carboxy or reactive functionally modified carboxy, is condensed with a compound of the formula

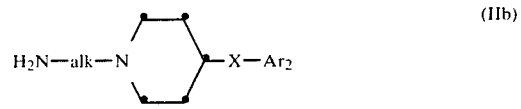

or with a salt thereof, or (b) compounds of the formulae

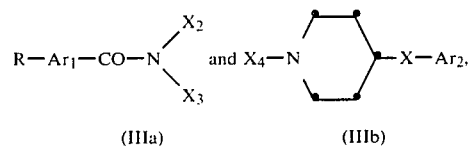

in which X$_2$ represents hydrogen, one of the radicals X$_3$ and X$_4$ represents hydrogen and the other radical represents a group of the formula —alk—X$_5$ and X$_5$ represents reactive esterified hydroxy, or, for the manufacture of compounds of the formula (I) in which alk represents 2- or 3-membered alkylene having from 2 up to and including 7 carbon atoms, compounds of the formulae (IIIa) and (IIIb) in which X$_2$ and X$_3$ together represent alk' wherein alk' represents 2- or 3-membered alkylene having from 2 up to and including 7 carbon atoms, and X$_4$ represents hydrogen, or the salts thereof, are intermolecularly condensed, or a compound of the formula

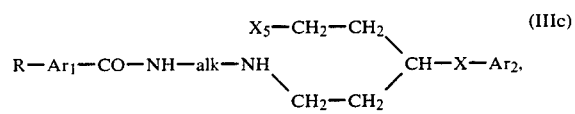

in which X$_5$ represents reactive esterified hydroxy, is intramblecularly condensed, or (c) for the manufacture of compounds of the formula (I) in which alk represents an alkylene group that has from 2 up to and including 7 carbon atoms and separates the two N atoms by 2 or 3 carbon atoms, a compound of the formula

in which alk' represents an alkylene group that has from 2 up to and including 7 carbon atoms and separates the C atom and N atom by 2 or 3 carbon atoms, is reacted with a compound of the formula

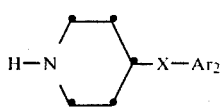

(IVb)

or (d) in a compound of the formula

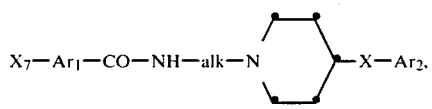

(V)

or in a salt thereof, in which $X_7$ represents a radical that can be converted into R, $X_7$ is converted into R, and, if desired, a compound obtainable in accordance with the process or in a different way is converted into a different compound according to the invention, and/or a salt obtainable in accordance with the process is converted into the free compound or into a different salt, and/or a free compound having salt-forming properties which is obtainable in accordance with the process is converted into a salt, and/or a mixture of isomers obtainable in accordance with the process is separated into the individual isomers.

Regarding variant (a):

Reactive functionally modified carboxy $X_1$ is, for example, esterified, especially reactive esterified, carboxy, anhydridised carboxy or amidated carboxy.

Esterified carboxy is, for example, optionally substituted lower alkoxycarbonyl, such as ethoxycarbonyl, but is preferably reactive esterified carboxy, for example vinyloxycarbonyl that is optionally additionally activated, for example by lower alkoxy or optionally substituted carbamoyl, such as 1-lower alkoxyvinyloxycarbonyl, for example 1-ethoxyvinyloxycarbonyl, or 2-(N-lower alkylcarbamoyl)vinyloxycarbonyl, for example 2-(N-ethylcarbamoyl)vinyloxycarbonyl, and phenoxycarbonyl or thiophenoxycarbonyl each of which is optionally substituted, for example, by nitro, halogen, lower alkanesulphonyl or phenylazo, such as 4-nitro-, 2,4,5-trichloro-, pentachloro-, 4-methanesulphonyl-, 4-phenylazophenoxycarbonyl, thiophenoxy- or 4-nitrothiophenoxycarbonyl, and likewise activated methoxycarbonyl, for example methoxycarbonyl substituted by cyano or also by optionally esterified carboxy, especially cyanomethoxycarbonyl. Reactive esterified carboxy can likewise be 1,1- or 1,3-disubstituted 2-isoureidocarbonyl, such as 1,1-di-lower alkyl-, 1,1-diaryl- or 1,1-diaryl-lower alkyl-2-isoureidocarbonyl, for example 1,1-diethyl-, 1,1-diphenyl- or 1,1-dibenzyl-2-isoureidocarbonyl, or 1,3-dicycloalkyl-2-isoureidocarbonyl, for example 1,3-dicyclohexyl-2-isoureidocarbonyl, or N-alkyleneaminooxycarbonyl, such as N-piperidinyloxycarbonyl, and also N-imido-oxycarbonyl, for example N-succinimidooxycarbonyl or N-phthalimido-oxycarbonyl.

There is to be understood by anhydridised carboxy, for example, optionally branched lower alkoxycarbonyloxycarbonyl, such as ethoxy- or isobutoxy-carbonyloxycarbonyl, halocarbonyl, such as chlorocarbonyl, azidocarbonyl, halophosphoryloxycarbonyl, such as dichlorophosphoryloxycarbonyl, or lower alkanoyloxycarbonyl optionally substituted, for example, by halogen or aryl, such as pivaloyloxycarbonyl, trifluoroacetoxycarbonyl or phenylacetoxycarbonyl. Anhydridised carboxy can also be symmetrically anhydridised carboxy of the formula $R-Ar_1-CO-O-CO-$.

Reactive amidated carboxy is, for example, 1-imidazolylcarbonyl or 1-pyrazolylcarbonyl each of which is optionally substituted, for example, by lower alkyl, such as 3,5-dimethylpyrazolylcarbonyl.

The condensation (N-acylation) in accordance with the process is carried out in a manner known per se, if necessary in the presence of a condensation agent, especially a basic condensation agent. As bases there come into consideration, for example, alkali metal hydroxides, hydrides, amides, alkoxides, carbonates, triphenylmethylides, di-lower alkylamides, aminoalkylamides or lower alkylsilylamides, naphthaleneamines, lower alkylamines, basic heterocycles, ammonium hydroxides and also carbocyclic amines. By way of example there may be mentioned sodium hydroxide, hydride or amide, potassium tert.-butoxide or carbonate, lithium triphenylmethylide or diisopropylamide, potassium 3-(aminopropyl)-amide or bis(trimethylsilyl)-amide, dimethylaminonaphthalene, di- or tri-ethylamine, or ethyldiisopropylamine, N-methylpiperidine, pyridine, benzyltrimethylammonium hydroxide, 1,5-diazabicyclo-[4.3.0]non-5-ene (DBN) and 1,8-diazabicyclo[5.4.0]undec-7-ene (DBU), and also phosphines, such as triphenylphosphine, or halosilanes, such as tetrachlorosilane. If $X_1$ represents carboxy, there are primarily formed the corresponding ammonium salts which can be dehydrated by heating or by treatment with suitable dehydrating agents, such as carbodiimides, for example N,N'-di-lower alkyl or N,N'-dicycloalkyl carbodiimide, such as N,N'-diethyl, N,N'-diisopropyl or N,N'-dicyclohexyl carbodiimide, advantageously with the addition of N-hydroxysuccinimide or optionally substituted, for example halo-, lower alkoxy- or lower alkyl-substituted, 1-hydroxybenzotriazole or N-hydroxy-5-norbornene-2,3-dicarboxamide, and also N,N-carbonyldiimidazole. Using carbodiimides there may be formed intermediately, for example, also the corresponding 1-isoureidocarbonyl compounds. As water-binding condensation agents there may furthermore be used N-ethoxycarbonyl-2-ethoxy-1,2-dihydroquinoline, phosphoryl cyanamides or phosphoryl azides, such as diethylphosphoryl cyanamide or diphenylphosphoryl azide, triphenylphosphine disulphide or 1-lower alkyl-2-halopiperidinium halides, such as 1-methyl-2-chloropyridinium iodide.

The N-acylation is carried out in a manner known per se, for example in the absence or, usually, in the presence of a suitable solvent or diluent or a corresponding mixture, while cooling, at room temperature or while heating, for example in a temperature range of from approximately $-20°$ C. to approximately $150°$ C., preferably from approximately $0°$ C. to approximately $100°$ C., and, if necessary, in a closed vessel, optionally under pressure and/or in an inert gas atmosphere.

The starting materials used in this process variant are in some cases known or can be manufactured by processes known per se.

For the manufacture of compounds of the formula (IIa) in which $X_1$ represents optionally substituted lower alkoxycarbonyl, the free acid ($X_1$=carboxy) or an acid anhydride ($X_1$ represents, for example, halocarbonyl) can usually be used as starting material and is reacted, for example, with the corresponding alcohol which is, if necessary, in reactive form, for example a lower alkyl halide. The manufacture of compounds of the formula (IIa) in which X₁ represents optionally additionally activated vinyloxycarbonyl can be effected, for example, by transesterification of a lower alkyl ester with vinyl acetate (activated vinyl ester method), by reaction of the free acid of compounds of the formula (IIa) with a lower alkoxyacetylene (for example ethoxyacetylene method) or, analogously to the Woodward method, with a 1,2-oxazolium salt. Compounds of the formula (IIa) containing optionally substituted phenoxycarbonyl or thiophenoxycarbonyl can be obtained, for example, starting from the free acid, according to the carbodiimide method, by reaction with the corresponding (thio-)phenol. Likewise starting from the free acid of the formula (IIa), it is possible to obtain compounds of the formula (IIa) in which X₁ represents activated methoxycarbonyl or 1,1- or 1,3-disubstituted 2-isoureidocarbonyl, for example by reaction with a haloacetonitrile, such as chloroacetonitrile (cyanomethyl ester method) or with a carbodiimide or cyanamide (carbodiimide or cyanamide method), respectively. N-alkyleneaminooxycarbonyl and N-imidooxycarbonyl compounds of the formula (IIa) can be manufactured, for example when using the free acid of the formula (IIa), from corresponding N-hydroxy compounds with the aid of carbodiimides according to the activated N-hydroxy esters method. For the manufacture of compounds of the formula (IIa) in which X₁ represents optionally branched lower alkoxycarbonyloxycarbonyl, halophosphoryloxycarbonyl or optionally substituted lower alkanoyloxycarbonyl, for example the free acid of the formula (IIa) can be used as starting material and is respectively treated, for example, with a corresponding halide, such as an optionally substituted lower alkylcarbonic acid halide (mixed 0-carbonic acid anhydrides method), phosphorus oxyhalide (for example, phosphorus oxychloride method) or optionally substituted lower alkanoyl halide (mixed carboxylic acid halides method). Azidocarbonyl compounds of the formula (IIa) are obtainable, for example, by treatment of corresponding hydrazides with nitrous acid (azide method). For the manufacture of compounds of the formula (IIa) in which X₁ represents optionally substituted 1-imidazolylcarbonyl or 1-pyrazolylcarbonyl, the free acid of the formula (IIa) is reacted, for example, with di-(1-imidazolyl)carbonyl (imidazolide method) or the relevant hydrazide, for example with a corresponding 1,3-diketone (pyrazolide method), respectively.

The starting material of the formula (IIb) in which X represents a carbonyl group can be obtained, for example, by acylating a compound of the formula Ar₂—H (IIc) with piperidine-4-carboxylic acid or a reactive derivative thereof analogously to a Friedel-Crafts acylation in the presence of a Lewis acid. The resulting compound of the formula

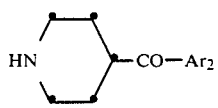

(IId)

can be converted into the corresponding compound of the formula (IIb), for example, by treatment with a compound of the formula Hal—alk—NH₂ (IIe), in which Hal represents halogen, such as bromine, for example in the presence of a base. The reduction of the carbonyl group X to the hydroxymethylene group X can be effected, starting from compounds of the formula (IId) or (IIb), for example with the aid of a suitable metal hydride, for example lithium aluminium hydride or sodium borohydride, and the reductive conversion of the carbonyl group via the hydroxymethylene group into the methylene group X can be effected, for example, by catalytic hydrogenation in the presence of a hydrogenation catalyst.

Compounds of the formula (IIb) in which X represents methylene can likewise be obtained by converting the carbonyl group in a compound of the formula (IId) into the methylene group, for example by catalytic hydrogenation, condensing the resulting compound with a haloacetonitrile, such as chloroacetonitrile, in the presence of a base, such as ethyldiisopropylamine and then converting the cyano group, for example by catalytic hydrogenation, into the aminomethylene group.

Regarding variant (b):

Reactive esterified hydroxy X₅ is especially hydroxy esterified by a strong inorganic acid or organic acid, for example halogen, such as chlorine, bromine or iodine, sulphonyloxy, such as hydroxysulphonyloxy, halosulphonyloxy, for example fluorosulphonyloxy, lower alkanesulphonyloxy optionally substituted, for example, by halogen, for example methane- or trifluoromethanesulphonyloxy, cycloalkanesulphonyloxy, for example cyclohexanesulphonyloxy, or benzenesulphonyloxy optionally substituted, for example, by lower alkyl or halogen, for example p-bromophenyl- or p-toluene-sulphonyloxy, lower alkanoyloxy optionally substituted, for example, by halogen, such as acetoxy or trifluoroacetoxy, or benzoyloxy optionally substituted, for example, by lower alkyl, lower alkoxy, halogen and/or by nitro.

The condensation (N-alkylation) in accordance with the process is carried out in a manner known per se, if necessary in the presence of a base. As bases there come into consideration, for example, alkali metal hydroxides, hydrides, amides, alkoxides, carbonates, triphenylmethylides, di-lower alkylamides, aminoalkylamides or lower alkylsilylamides, naphthaleneamines, lower alkylamines, basic heterocycles, ammonium hydroxides and also carbocyclic amines. By way of example there may be mentioned sodium hydroxide, hydride or amide, potassium tert.-butoxide or carbonate, lithium triphenylmethylide or diisopropylamide, potassium 3-(aminopropyl)-amide or bis(trimethylsilyl)-amide, dimethylaminonaphthalene, di- or tri-ethylamine, or ethyldiisopropylamine, N-methylpiperidine, pyridine, benzyltrimethylammonium hydroxide, 1,5-diazabicyclo[4.3.0]non-5-ene (DBN) and 1,8-diazabicyclo[5,4,0]undec-7-ene (DBU), and also phosphines, such as triphenylphosphine, or halosilanes, such as tetrachlorosilane.

The N-alkylation is carried out, for example, in the absence or, usually, in the presence of a suitable solvent or diluent or a corresponding mixture, at room temperature or while heating, for example in a temperature range of from approximately 0° C. to approximately 200° C., preferably between room temperature and approximately 150° C., and, if necessary, in a closed vessel, optionally under pressure and/or under an inert gas.

The starting materials used in this process variant are partly known or can be manufactured according to processes known per se.

For example, starting materials of the formula (IIIa) in which $X_2$ represents hydrogen and $X_3$ represents a group of the formula —alk—$X_5$ are obtainable, for example, by starting from a carboxylic acid of the formula R—$Ar_1$—COOH (IIId) or a reactive acid derivative, especially a carboxylic acid halide, thereof and treating it with an amine of the formula $X_5$—alk—$NH_2$ (IIIe). Starting materials of the formula (IIIa) in which $X_2$ and $X_3$ together represent alk', wherein alk' represents 2- or 3-membered alkylene having from 2 up to and including 7 carbon atoms, especially ethylene, can be manufactured, for example, by N-acylating a corresponding aziridine or azetidine with a compound of the formula (IIId) or a reactive acid derivative thereof, for example in the presence of a base, for example triethylamine. Starting materials of the formula (IIIa) in which $X_2$ and $X_3$ represent hydrogen are obtainable, for example, from corresponding compounds of the formula (IIId) or reactive derivatives thereof by reaction with ammonia.

For the manufacture of starting materials of the formula (IIIb) or salts thereof in which $X_4$ represents a group of the formula —alk—$X_5$, there are used as starting materials, for example, compounds of the formula (IIIb) in which $X_4$ represents hydrogen and, first of all, under customary N-alkylating conditions, for example in the presence of a base, such as triethylamine, there is introduced, by treating with an ethylene oxide or a propylene oxide or a compound of the formula $X_5$—alk—OH (IIIf), the group —alk—OH in which the hydroxy group is subsequently reactively esterified.

The starting material of the formula (IIIc) is obtainable, for example, by reacting compounds of the formulae R—$Ar_1$—CO—NH—alk—$NH_2$ and (IIIg)

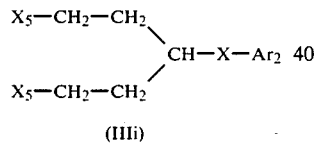

(IIIi)

in the presence of a base that is customary for N-alkylation, for example one of the bases mentioned above, such as pyridine, with one equivalent of H—$X_5$ being removed. Depending on the reaction conditions chosen, for example the concentration ratios, the N-alkylation may result directly in situ in the corresponding desired compounds of the formula (I), with a further equivalent of H—$X_5$ being removed.

Compounds of the formula (IIIg) in their turn or salts thereof can be obtained, for example, by amidating a compound of the formula (IIId) or a reactive acid derivative thereof, under customary conditions, with an excess of a compound of the formula $H_2N$—alk—$NH_2$ (IIIh). Compounds of the formula (IIIi) can be manufactured, for example, by reacting a compound of the formula $X_6$—$CH_2$—$CH_2$—$CH_2$—CO—$Ar_2$ (IIIj) in which $X_6$ represents, for example, alkoxy, under base catalysis, for example in the presence of sodium amide, with ethylene oxide and subsequently cleaving the ether. The ether can be cleaved, for example, with the aid of a Lewis acid, such as boron trifluoride, or a strong hydrohalic acid, such as hydrobromic or hydriodic acid. If a hydrohalic acid is chosen, which is used in excess, it is possible to obtain compounds of the formula (IIIi) in which X represents the carbonyl group and $X_5$ represents halogen. If desired, the carbonyl group X can be converted in customary manner by reduction into the hydroxymethylene or methylene group.

Regarding variant (c):

The reaction in accordance with the process is carried out in a manner known per se, if necessary in the presence of a base. As bases there come into consideration, for example, alkali metal hydroxides, hydrides, amides, alkoxides, carbonates, triphenylmethylides, di-lower alkylamides, aminoalkylamides or lower alkylsilylamides, naphthaleneamines, lower alkylamines, basic heterocycles, ammonium hydroxides and also carbocyclic amines. By way of example there may be mentioned sodium hydroxide, hydride or amide, potassium tert.-butoxide or carbonate, lithium triphenylmethylide or diisopropylamide, potassium 3-(aminopropyl)-amide or bis-(trimethylsilyl)-amide, dimethylaminonaphthalene, di- or tri-ethylamine, or ethyldiisopropylamine, N-methylpiperidine, pyridine, benzyltrimethylammonium hydroxide, 1,5-diazabicyclo[4.3.0]non-5-ene (DBN) and 1,8-diazabicyclo[5,4,0]undec-7-ene (DBU), and also phosphines, such as triphenylphosphine, or halosilanes, such as tetrachlorosilane.

The reaction is carried out in a manner known per se, for example in the absence or, usually, in the presence of a suitable solvent or diluent or a corresponding mixture, while cooling, at room temperature or while heating, for example in a temperature range of from approximately −20° C. to approximately 200° C., preferably between room temperature and approximately 150° C., and, if necessary, in a closed vessel, optionally under pressure and/or under an inert gas.

The starting materials used in this process variant are in some cases known or can be manufactured according to processes known per se.

For example, starting materials of the formula (IVa) can be obtained by starting from, for example, a carboxylic acid of the formula R—$Ar_1$—COOH (IIId) or a reactive acid derivative, especially an acid halide, thereof and first of all treating with an amine of the formula $X_5$—alk'—$NH_2$ (IVc) in which $X_5$ represents reactive esterified hydroxy, and then treating the resulting carboxylic acid amide of the formula

in which $X_2$ represents hydrogen and $X_3$ represents a group of the formula —alk'—$X_5$, with a base, for example triethylamine or ethyldiisopropylamine.

Regarding variant (d):

A radical $X_7$ that can be converted into R is, for example, a diazonium grouping of the formula —$N_2$-⊕A⊖, in which A⊖ represents the anion of a strong protonic acid, for example an anion of a mineral acid or complex metal acid, such as chloride, perchlorate, sulphate, tetrafluoroborate or hexachloroantimonate.

The substitution of the diazonium group $X_7$ in compounds of the formula (V) by hydroxy can be effected analogously to "phenol concentration by boiling" in aqueous medium, whilst treatment of the diazonium salt of the formula (V) with an aliphatic alcohol, especially with a lower alkanol, can result in compounds of the formula (I) in which R represents hydroxy etherified by an aliphatic alcohol.

The replacement of $X_7$ in compounds of the formula (V) by chlorine, bromine or iodine can be effected, for example, by reaction with corresponding halides, such as alkali metal halides. In this operation, there is present as the anion $A^\ominus$ the halide corresponding to the particular halogen atom. The reaction can be catalysed, for example, analogously to the Sandmeyer reaction by Cu(I) ions, according to the Gattermann reaction by copper powder or in the manner of the Körner-Contardi reaction by Cu(II) ions. In order to introduce fluorine into corresponding compounds of the formula (V), for example, according to the Schiemann reaction, it is possible to start from diazonium salts of the formula (V) which are reacted with fluoboric acid or a salt, especially an alkali metal salt, thereof, or, as a modification of that reaction, with corresponding pentafluorosilicates or hexafluorophosphates. In this operation, the resulting salt containing the particular diazonium-fluorine complex, especially in the dry state, is first of all thermally decomposed to a compound of the formula (I) in which R represents fluorine.

The substitution of the grouping $X_7$ can be carried out in a manner known per se, if necessary in the presence of a solvent or diluent, at reduced or elevated temperature, for example in a range of from approximately 40° to approximately 120° C., and/or in a closed vessel.

For the manufacture of the starting material of the formula (V) in which $X_7$ represents the ionic grouping $-N_2^\oplus A^\ominus$, for example, it is possible to start from compounds of the formula

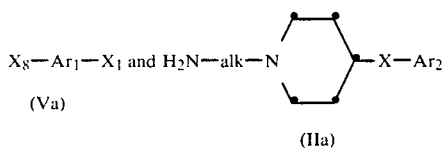

in which $X_1$ has the meaning given above and $X_8$ represents an amino group which is optionally protected, for example advantageously by a readily removable acyl group, and these compounds are condensed, for example in the manner described under variant (a), and the amino-protecting group which may be present is removed again. In resulting compounds of the formula

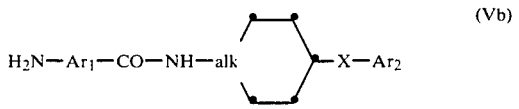

the amino group can be converted into the corresponding ionic grouping $X_7$ in a manner known per se by customary diazotisation, for example with nitrous acid or a nitrite in the presence of an acid.

The diazotisation of the aromatic amino compound (Vb) and the subsequent conversion of resulting compounds of the formula (V) into compounds of the formula (I) are advantageously carried out in situ without isolating the corresponding starting material of the formula (V). The isolation thereof is advisable, however, for the process variant analogous to the Schiemann reaction.

A radical $X_7$ that can be converted into R can furthermore be an acyloxy radical derived from an organic carboxylic acid, acyloxy being, for example, lower alkanoyloxy or aroyloxy each of which is optionally substituted, for example, by halogen or aryl, such as optionally substituted benzoyloxy.

The conversion of corresponding compounds of the formula (V) into compounds of the formula (I) in which R represents hydroxy is effected, for example, by hydrolysis or transesterification, each operation being carried out in the presence of an acid or a base. In these operations, hydroxy groups esterified by an aliphatic alcohol may, if they are substituents of the aromatic systems $Ar_1$ and/or $Ar_2$, be correspondingly hydrolysed or transesterified at the same time.

Starting from corresponding compounds of the formula (V), it is possible to obtain, for example by reaction with a reactive ester of an aliphatic alcohol, for example with a lower alkyl halide or sulphonate, compounds of the formula (I) in which R represents hydroxy etherified by an aliphatic alcohol. The reaction is advantageously carried out in the presence of a base. In the course of this reaction, hydroxy groups esterified by an organic carboxylic acid that are substituents of the aromatic radicals $Ar_1$ and/or $Ar_2$ can, at the same time, be converted into hydroxy groups etherified by an aliphatic alcohol.

A radical $X_7$ that can be converted into R can also be protected hydroxy, for example hydroxy protected by a hydroxy-protecting group customarily used in the relevant literature, protected hydroxy being, for example, 1-aryl-lower alkoxycarbonyloxy, such as benzyloxycarbonyloxy optionally substituted in the phenyl ring, for example by halogen, 1-aryl-lower alkoxy, such as benzyloxy optionally substituted in the phenyl moiety, for example by halogen or lower alkoxy, or silyloxy, such as optionally substituted tri-lower alkylsilyloxy. Corresponding preferred radicals $X_7$ are, for example, benzyloxycarbonyloxy, 2- or 4-bromobenzyloxycarbonyloxy, benzyloxy, 3-bromo-, 2,6-dichloro- or 4-methoxy-benzyloxy or trimethylsilyloxy.

Such radicals $X_7$ can be converted into hydroxy R in a manner known per se, for example by hydrolysis, acidolysis or reduction.

The hydrolytic removal of the hydroxy-protecting group can optionally be effected in the presence of a base or acid that supports hydrolysis, there being suitable as bases, for example, alkali metal or alkaline earth metal hydroxides or carbonates and, as acids, for example, inorganic or organic protonic acids.

1-aryl-lower alkoxycarbonyloxy or silyloxy radicals are preferably converted into hydroxy by hydrolysis.

In the case of acidolysis, as a rule strong acids, such as mineral acids, for example hydrohalic acids, perchloric acid, optionally suitably substituted lower alkanecarboxylic acids or sulphonic acids, such as optionally substituted benzenesulphonic acids, or mixtures thereof are used.

Preferred acids are, for example, hydrofluoric acid, hydrobromic acid/glacial acetic acid or trifluoroacetic acid.

Groups that can be converted correspondingly into hydroxy R are, for example, 1-aryl-lower alkoxycarbonyloxy or 1-aryl-lower alkoxy.

These radicals can be converted into hydroxy also by reduction, for example by hydrogenolysis with hydrogen in the presence of a hydrogenation catalyst, and 1-aryl-lower alkoxycarbonyloxy can be converted into hydroxy, in addition, by reduction with metallic systems comprising a metal component and a hydrogen-yielding component, such as sodium/ammonia.

These reactions can be carried out in a manner known per se, if necessary in the presence of a solvent or diluent, at reduced or, especially, at elevated temperature, in a temperature range of from approximately 50° to approximately 150° C., in a closed vessel and/or under an inert gas.

The starting material of the formula (V) in which $X_7$ represents an acyloxy radical or protected hydroxy can be obtained by condensing, for example, a compound of the formula $$X_7-Ar_1-X_1 \qquad (Vd)$$

with a compound of the formula (IIa), analogously to the method given under variant (a).

A compound according to the invention which is obtainable in accordance with the process or in a different way can be converted in a manner known per se into a different compound according to the invention.

For example, in the compounds according to the invention that contain a free hydroxy group and/or a hydroxymethylene group the hydroxy group can be esterified by an organic carboxylic acid, such as a lower alkanecarboxylic acid. This esterification is carried out in a manner known per se, for example by treatment with the desired carboxylic acid or a reactive derivative, for example an acid anhydride or halide, if necessary in the presence of an acid, such as a protonic acid, for example a mineral acid or sulphonic acid, or a Lewis acid, for example corresponding halides of suitable elements of the 3rd main group or the corresponding sub-groups.

The esterification can also proceed in the presence of a base, such as an alkali metal hydroxide or carbonate, or an amine, or a cyclic nitrogen base, or a water-binding agent, such as a customary carbodiimide. Conversely, in groups having esterified hydroxy, the hydroxy group can be freed by solvolysis, for example with the aid of base catalysis.

The corresponding reactions may, if necessary, be carried out while cooling or heating, for example in a temperature range of from approximately 0° to approximately 100° C., in the presence or absence of a solvent or diluent, under an inert gas and/or under pressure and optionally in a closed vessel.

A compound according to the invention that contains hydroxy can be etherified according to methods known per se. The etherification can be effected, for example, with an alcohol, such as an optionally substituted lower alkanol, or a reactive ester thereof. As reactive esters of the desired alcohols there come into consideration, for example, those with strong inorganic or organic acids, such as corresponding halides, sulphates, lower alkanesulphonates or optionally substituted benzenesulphonates, for example chlorides, bromides or iodides, or methane-, benzene- or p-toluene-sulphonates. The etherification can be carried out, for example, in the presence of a base, an alkali metal hydride, hydroxide or carbonate, or a basic amine. Conversely, corresponding ethers, such as lower alkoxy compounds, can be cleaved, for example, by means of strong acids, such as mineral acids, for example the hydrohalic acids hydrobromic or hydriodic acid which may advantageously be in the form of pyridinium halides, or by means of Lewis acids, for example halides of elements of the 3rd main group or the corresponding sub-groups. These reactions may, if necessary, be carried out while cooling or heating, for example in a temperature range of from approximately −20° to approximately 100° C., in the presence or absence of a solvent or diluent, under an inert gas and/or under pressure and optionally in a closed vessel.

In a compound according to the invention having a hydroxy-lower alkyl radical, the hydroxy group can be converted into halogen, for example chlorine, for example by treatment with a suitable halogenation agent, for example thionyl chloride.

If the aryl radicals $Ar_1$ and/or $Ar_2$ have, for example, a cyano group as substituent, the cyano group can be converted into a carbamoyl group, for example by hydrolysis, preferably under acidic or basic conditions, for example in the presence of an alkali metal hydroxide, and, if desired, in the presence of hydrogen peroxide in an aqueous-alcoholic solvent. Such reactions may, if necessary, be carried out while cooling or heating, for example in a temperature range of from approximately 0° to approximately 150° C., occasionally also at higher temperatures, in the presence or absence of a solvent or diluent, under an inert gas and/or under pressure and, optionally, in a closed vessel.

If the radicals $Ar_1$ and/or $Ar_2$ in compounds according to the invention have cyano as substituent, the cyano group can be converted, for example, into alkoxycarbonyl, for example by treatment with an alcohol, for example a lower alkanol, in the presence of an acid, for example hydrochloric acid.

In compounds of the formula (I) in which $Ar_1$ and/or $Ar_2$ have an esterified or amidated carboxy group as substituent, such a group can be converted into a free carboxy group, for example by means of hydrolysis, for example in the presence of a basic agent, such as an inorganic base, for example an alkali metal or alkaline earth metal hydroxide, for example sodium, potassium or calcium hydroxide, or an acidic agent, such as a mineral acid.

In compounds of the formula (I) in which $Ar_1$ and/or $Ar_2$ have a carboxy group as substituent, the carboxy group can also be converted into an esterified carboxy group, for example by treatment with an alcohol, such as a lower alkanol, in the presence of a suitable esterification agent, such as an acidic reagent, for example an inorganic or organic acid, such as hydrochloric, trifluoroacetic or p-toluenesulphonic acid, or a Lewis acid, for example zinc chloride, or a water-binding condensation agent, for example a carbodiimide, such as N,N'-dicyclohexyl carbodiimide, or by treatment with a diazo reagent, such as a diazo-lower alkane, for example diazomethane. The esterified carboxy group can also be obtained if compounds of the formula I in which a carboxy group is present as substituent in $Ar_1$ and/or $Ar_2$ in free form or in the form of a salt, such as an ammonium salt or a metal salt, for example an alkali metal salt, such as a sodium or potassium salt, are treated with a reactive ester of an alcohol, such as a lower alkyl halide, for example methyl or ethyl chloride, bromide or iodide, or with an organic sulphonic acid ester, such as a corresponding lower alkyl ester, for example methanesulphonic acid methyl or ethyl ester or p-toluenesulphonic acid methyl or ethyl ester.

Compounds of the formula (I) in which $Ar_1$ and/or $Ar_2$ have as substituent an esterified carboxy group can be converted into other ester compounds of the formula (I) by transesterification, for example by treatment with an alcohol, usually an alcohol higher than that corresponding to the esterified carboxy group in the starting material, in the presence of a suitable transesterification agent, such as a basic agent, for example an alkali metal lower alkanoate, lower alkoxide or cyanide, such as sodium acetate, methoxide, ethoxide, tert.-butoxide or cyanide, or a suitable acidic agent, optionally with the removal of the alcohol produced, for example by distillation. It is also possible to start from corresponding, so-called activated esters of the formula (I) in which $Ar_1$ and/or $Ar_2$ have as substituent an activated esterified carboxy group (see below), and to convert these by treatment with an alcohol, such as a lower alkanol, into a different ester.

Compounds of the formula (I) in which $Ar_1$ and/or $Ar_2$ have as substituent an amidated carboxy group can advantageously be obtained also from the corresponding acid or ester compounds of the formula (I) in which $Ar_1$ and/or $Ar_2$ have as substituent an optionally esterified carboxy group. For example, it is possible to react compounds of the formula (I) having a free carboxy group with urea at elevated temperatures, for example at 200°–240° C., with a formamide, for example dimethylformamide, in the presence of a suitable condensation agent, such as phosphorus pentoxide, at elevated temperatures, or with an amine in the presence of a suitable condensation agent, such as a carbodiimide, for example N,N'-diethyl carbodiimide, or in the presence of a phosphine, such as triphenylphosphine (for example together with bis-2-pyridyl disulphide), or a silane, such as trichlorosilane (for example together with pyridine), and obtain the corresponding amide compounds of the formula (I) in which $Ar_1$ and/or $Ar_2$ contain as substituent an amidated carboxy group. They can also be obtained from compounds of the formula (I) in which $Ar_1$ and/or $Ar_2$ have as substituent a carboxy group in salt form, for example by dehydrating a corresponding ammonium salt, for example by treatment with a dehydrating agent, such as phosphorus pentoxide, or by reacting a corresponding alkali metal salt, for example a sodium salt, with an amine, preferably in the presence of a suitable condensation agent, such as phenylphosphonic acid dichloride.

In compounds of the formula (I) in which $Ar_1$ and/or $Ar_2$ contain as substituent a carboxy group, this group can also first of all be converted into a reactive derivative, such as an anhydride, including a mixed anhydride, such as an acid halide, for example acid chloride (for example by treatment with a thionyl halide, for example thionyl chloride), or an anhydride with a formic acid ester, for example a formic acid lower alkyl ester (for example by treating a salt, such as an ammonium or alkali metal salt, with a haloformic acid ester, such as a chloroformic acid ester, such as a chloroformic acid lower alkyl ester), or into an activated ester, such as a cyanomethyl, nitrophenyl, for example 4-nitrophenyl, or polyhalophenyl, for example pentachlorophenyl, ester (for example by treatment with a corresponding hydroxy compound in the presence of a suitable condensation agent, such as N,N'-dicyclohexyl carbodiimide), and then such a reactive derivative can be reacted with ammonia (optionally in the form of a derivative) or an amine and there can thus be obtained amide compounds of the formula (I) in which $Ar_1$ and/or $Ar_2$ have as substituent an amidated carboxy group. These compounds can be obtained directly or by way of intermediates; for example, an activated ester, such as a 4-nitrophenyl ester, of a compound of the formula I having a carboxy group can first be reacted with a 1-unsubstituted imidazole, and the resulting 1-imidazolylcarbonyl compound can be reacted with the ammonia or the amine. It is, however, also possible to react other, non-activated esters, such as lower alkyl esters of compounds of the formula (I) in which $Ar_1$ and/or $Ar_2$ have as substituent, for example, lower alkoxycarbonyl, with ammonia or amines.

In compounds according to the invention in which the radical $Ar_1$ and/or $Ar_2$ contain a free amino, carbamoyl or sulphamoyl group, the particular amino group can be mono- or di-substituted in the manner given above under variant (b). Primary or secondary amino groups can likewise be alkylated by reduction, analogously to the Leuckart-Wallach (or Eschweiler-Clarke) reaction, from carbonyl compounds, for example using formic acid as reducing agent.

In compounds according to the invention in which X represents a carbonyl group, this group can be converted into a hydroxymethylene group X, for example by reduction, for example by treatment with a suitable, optionally complex, hydride, such as a hydride formed from an element of Groups 1 and 3 of the Periodic Table of Elements, for example sodium borohydride or sodium cyanoborohydride. The hydroxymethylene group X can in turn be reduced to the methylene group, for example by reduction, for example with hydrogen using a hydrogenation catalyst.

In compounds according to the invention in which X represents the carbonyl group, this group can be acetalised, for example in the presence of an acid, such as a mineral acid, for example sulphuric or hydrochloric acid, or sulphonic acid, for example p-toluenesulphonic acid, with an alcohol, such as a lower alkanol or a lower alkanediol, for example ethanol or glycol. Acetalised carbonyl X can, for example, conversely be hydrolysed by acids, for example of the kind mentioned above.

If the ring $Ar_1$ is substituted by lower alkylthio, the latter can be oxidised in customary manner to corresponding lower alkanesulphinyl or lower alkanesulphonyl. As suitable oxidising agents for the oxidation to the sulphoxide stage there come into consideration, for example, inorganic peracids, such as peracids of mineral acids, for example periodic acid or persulphuric acid, organic peracids, such as corresponding percarboxylic or persulphonic acids, for example performic, peracetic or trifluoroperacetic acid or perbenzoic or p-toluenepersulphonic acid, or mixtures of hydrogen peroxide and acids, for example a mixture of hydrogen peroxide and acetic acid.

The oxidation is frequently carried out in the presence of suitable catalysts, there being mentioned as catalysts suitable acids, such as optionally substituted carboxylic acids, for example acetic acid or trifluoroacetic acid, or transition metal oxides, such as oxides of elements of sub-group VII, for example vanadium, molybdenum or tungsten oxide. The oxidation is carried out under mild conditions, for example at temperatures of from approximately $-50°$ to approximately $+100°$ C.

The oxidation to the sulphone stage can be carried out correspondingly also with dinitrogen tetroxide as catalyst in the presence of oxygen at low temperatures, as can also the direct oxidation of lower alkylthio to lower alkanesulphonyl. In this case, however, the oxidising agent is usually used in excess.

If an aromatic ring ($Ar_1$ and/or $Ar_2$) has a hydrogen atom as substituent, the hydrogen atom can be replaced by a halogen atom with the aid of a halogenation agent in customary manner, for example brominated with bromine, hypobromic acid, acylhypobromite or other organic bromine compounds, for example N-bromosuccinimide, N-bromoacetamide, N-bromophthalimide, pyridinium perbromide, dioxan dibromide, 1,3-dibromo-5,5-dimethylhydantoin, 2,4,4,6-tetrabromo2,5-cyclohexanedien-1-one, or chlorinated with elemental chlorine, for example in a halogenated hydrocarbon, such as chloroform, and while cooling, for example to from approximately −10° to approximately +10° C.

Furthermore, the cyano group can be introduced into the ring $Ar_1$ by, for example, substituting a halogen atom, especially iodine or bromine, by a cyano group by reaction with a cyano compound, such as an alkali metal cyanide, for example potassium cyanide, or especially with Cu(I) cyanide, preferably while heating, for example to from approximately 60° to approximately 250° C., in the presence or absence of a solvent or diluent, or advantageously under an inert gas.

If the aryl radicals $Ar_1$ and/or $Ar_2$ in the compounds according to the invention contain an amino group, this group can be diazotised in customary manner, for example by treatment with a nitrite, for example sodium nitrite, in the presence of a suitable protonic acid, for example a mineral acid, the reaction temperature advantageously being maintained at below approximately 5° C. The diazonium group so obtained, which is in the form of a salt, can be substituted according to analogous methods, for example as follows: by the hydroxy group analogously to the phenol concentration by boiling, in the presence of water; by an alkoxy group by treatment with a corresponding alcohol, it being necessary to supply energy; by the fluorine atom analogously to the Schiemann reaction in the thermolysis of corresponding diazonium tetrafluoroborates; by the halogen atoms chlorine, bromine or iodine and the cyano group analogously to the Sandmeyer reaction in the reaction with corresponding Cu(I) salts, initially while cooling, for example to approximately below 5° C., and subsequently while heating, for example to from approximately 60° to approximately 150° C.

If the compounds according to the invention have a nitro group in the aryl radicals $Ar_1$ and/or $Ar_2$, this group can be reduced to the amino group in a manner known per se, for example by catalytic hydrogenation.

An aromatic ring $Ar_1$ and/or $Ar_2$ can also be alkylated, for example with a lower alkanol or a lower alkyl halide or a phosphoric acid lower alkyl ester in the presence of Lewis acids (Friedel-Crafts alkylation). In a compound of the formula (I) in which an aromatic ring contains bromine, for example, the bromine can be replaced by lower alkyl by reaction with a lower alkyl bromide in the presence of an alkali metal.

If an aromatic ring contains a hydrogen atom as substituent, the hydrogen atom can be exchanged for an acyl group in a manner known per se. For example, the introduction of the acyl group can be carried out analogously to the Friedel-Crafts acylation (cf. G. A. Olah, Friedel-Crafts and Related Reactions, vol. I, Interscience, New York, 1963-1965), for example by reacting a reactive functional acyl derivative, such as a halide or anhydride, of an organic carboxylic acid in the presence of a Lewis acid, such as aluminium, antimony(III), antimony(V), iron(III) or zinc(II) chloride or boron trifluoride.

If the compounds of the formula (I) contain unsaturated radicals, such as lower alkenyl or lower alkadienyl groupings, these can be converted into saturated radicals in a manner known per se. For example, the hydrogenation of multiple bonds is effected by catalytic hydrogenation in the presence of hydrogenation catalysts, there being suitable for this purpose, for example, noble metals or derivatives thereof, for example oxides, such as nickel, Raney nickel, palladium or platinum oxide which may optionally be applied to carriers, for example carbon or calcium carbonate. The hydrogenation can preferably be carried out at pressures of between 1 and approximately 100 atm and at a temperature between approximately −80° and approximately 200° C., especially between room temperature and approximately 100° C. The reaction is effected expediently in a solvent, such as water, a lower alkanol, for example ethanol, isopropanol or n-butanol, an ether, for example dioxan, or a lower alkanecarboxylic acid, for example acetic acid.

The invention relates especially to the processes described in the Examples.

If the starting materials mentioned have basic centres, for example, acid addition salts also may be formed, whilst starting materials with acidic groups, for example, form salts with bases.

Depending on the reaction conditions chosen, the starting materials may be used in free form or in the form of salts, and the compounds according to the invention having salt-forming properties may be obtained in free form or in the form of salts.

Resulting acid addition salts can, therefore, in a manner known per se, be converted into the free compounds, for example by treatment with a base, such as an alkali metal hydroxide, or into different salts, for example by treatment with suitable acids or derivatives thereof. Resulting free compounds having salt-forming properties can be converted into their salts, for example by treatment with acids or corresponding anion exchangers.

Owing to the close relationship between the salt-forming compounds in free form and in the form of salts, hereinbefore and hereinafter there is to be understood by the free compounds or their salts, where appropriate and expedient, optionally also the corresponding salts and free compounds, respectively. The invention relates also to salts that are unsuitable for pharmaceutical applications, since these may be used, for example, for the isolation or purification of free compounds according to the invention and their pharmaceutically acceptable salts.

The compounds according to the invention, including salts of corresponding salt-forming compounds, may also be obtained in the form of their hydrates, or their crystals may include, for example, the solvent used for crystallisation.

Depending on the starting materials and procedures chosen, the novel compounds may be in the form of one of the possible isomers or in the form of mixtures thereof: for example, depending on the number of asymmetric carbon atoms, in the form of pure optical isomers, such as antipodes, or in the form of mixtures of isomers, such as racemates, mixtures of diastereoisomers or mixtures of racemates.

Resulting mixtures of diastereoisomers and mixtures of racemates can be separated on the basis of the physical-chemical differences between the constituents, in known manner, into the pure isomers, diastereoisomers or racemates, for example by chromatography over chiral adsorbents and/or by fractional crystallisation. Resulting racemates can furthermore be resolved, according to known methods, into the optical antipodes, for example by recrystallisation from an optically active solvent, with the aid of microorganisms, by splitting with specific immobilised enzymes, by way of the formation of inclusion compounds, for example using chiral Crown ethers, with an enantiomer being complexed, or by conversion into diastereoisomeric salts or esters, for example by reacting a basic end product racemate with an optically active acid that forms salts with the racemic base, or with an optically active carboxylic acid or a reactive derivative thereof, and separating the mixture of diastereoisomers obtained in this manner, for example on the basis of their differing solubilities, into the diastereoisomers from which the desired enantiomers can be freed by the action of suitable agents. Advantageously, the more active enantiomer is isolated.

The invention relates also to those forms of the process according to which a compound obtainable as intermediate at any stage of the process is used as starting material and the remaining steps are carried out, or a starting material is used in the form of a derivative or salt and/or its racemates or antipodes or, especially, is formed under the reaction conditions.

In the process of the present invention, the starting materials used are preferably those which result in the compounds described at the beginning as being especially valuable. The invention relates also to novel starting materials developed specifically for the manufacture of the compounds according to the invention, their use, for example as intermediates, and also optionally as medicinal active ingredients, and to processes for the manufacture thereof, the variables R, $Ar_1$, alk, X and $Ar_2$ having the meanings preferred for the respectively preferred groups of compounds of the formula (I).

The dosage of the active ingredient, which is administered on its own or together with the customary carrier and adjunct, depends on the species to be treated, its age and individual condition and also on the mode of administration. Depending on the type of illness, individual condition and age, the single doses, for example for mammals having a body weight of approximately 70 kg, are preferably between approximately 0.5 and 100 mg, for example between approximately 0.7 and 70 mg, for example in the case of oral administration.

The invention relates further to processes for the manufacture of pharmaceutical preparations that contain, as active ingredients, compounds of the formula (I) or pharmaceutically acceptable salts of such compounds having salt-forming properties.

The pharmaceutical preparations according to the invention are those for enteral, such as peroral or rectal, administration and also for parenteral administration to warm-blooded animals. Corresponding unit dose forms, especially for peroral administration, for example dragées, tablets or capsules, contain preferably from approximately 1 mg to approximately 100 mg, especially from approximately 1 mg to approximately 25 mg, of a compound of the formula (I), or a pharmaceutically acceptable salt of a corresponding compound capable of salt-formation, together with pharmaceutically acceptable carriers.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores can be provided with suitable coatings that may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

Other orally administrable pharmaceutical preparations are dry-filled capsules made from gelatine, and also soft, sealed capsules made from gelatine and a plasticiser, such as glycerine or sorbitol. The dry-filled capsules may contain the active ingredient in the form of granules, for example in admixture with fillers, such as lactose, binders, such as starches and/or glidants, such as talc or magnesium stearate, and, optionally, stabilisers. In soft capsules, the active ingredient is preferably dissolved or suspended in suitable liquids, such as fatty oils, paraffin oil or liquid polyethylene glycols, it being possible also to add stabilisers. Preferred are, inter alia, capsules which can be both easily bitten through and also swallowed without chewing.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols or higher alkanols. There may also be used gelatine rectal capsules which contain a combination of the active ingredient with a base; as bases there come into consideration, for example, liquid triglycerides, polyethylene glycols or paraffin hydrocarbons.

Especially suitable for parenteral administration are aqueous solutions of an active ingredient in water-soluble form, for example solutions of a water-soluble salt, and also suspensions of the active ingredient, such as corresponding oily injection suspensions, with lipophilic solvents or vehicles, such as fatty oils, for example sesame oil, or synthetic fatty acid esters, for example ethyl oleate, or triglycerides being used, or aqueous injection suspensions which contain substances that increase the viscosity, for example sodium carboxymethylcellulose, sorbitol and/or dextran, and, optionally, stabilisers.

The pharmaceutical preparations of the present invention can be produced in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture and, if desired or necessary after the addition of suitable adjuncts, processing the mixture or granulate to form tablets or dragée cores.

The following Examples illustrate the invention described above but without limiting the scope thereof in any way. Temperatures are given in degrees Centigrade.

EXAMPLE 1

41.4 g (0.2 mol) of 4-(p-fluorobenzoyl)-piperidine are dissolved in 120 ml of dioxan, and 28.3 g (0.1 mol) of N-(2-bromoethyl)-5-cyano-2-methoxybenzamide are added and the whole is then stirred at room temperature for 60 hours. A solution of potassium carbonate is then added to the reaction mixture and the whole is then extracted with methylene chloride. The methylene chloride solution is washed neutral with water and concentrated in a water-jet vacuum. A light yellow crystalline product remains behind which is suspended in 200 ml of ethanol and stirred for 2 hours. The solid product is then filtered with suction and subsequently washed with 20 ml of ice-cold ethanol. 5-Cyano-N-[2-[4-(p-fluorobenzoyl)-piperidinyl]-ethyl]-2-methoxybenzamide is obtained in the filtration residue in the form of white powder of melting point 167°–169°.

To convert it into the hydrochloride, the free base is dissolved in methylene chloride, and an ethereal hydrogen chloride solution is added thereto until a Congo-acid reaction is obtained. Ether is then added until crystallisation begins. In this manner, there is obtained 5-cyano-N-[2-[4-(p-fluorobenzoyl)-piperidinyl]-ethyl]-2-methoxybenzamide hydrochloride of melting point 193°–194°.

The starting material is manufactured as follows:

64.6 g (0.5 mol) of ethyldiisopropylamine are added dropwise, while stirring at room temperature, to 39.1 g (0.2 mol) of crude 5-cyano-2-methoxybenzoic acid chloride, manufactured according to French Pat. No. 1.525 M/72 CAM and 45 g (0.22 mol) of 2-bromoethylamine hydrobromide in 300 ml of methylene chloride. The resulting clear solution is then stirred for a further 2 hours at room temperature. The methylene chloride solution is then extracted by shaking twice with 2N hydrochloric acid and once with water, dried over magnesium sulphate and concentrated by evaporation. For purification, the resulting N-(2-bromoethyl)-5-cyano-2-methoxybenzamide is recrystallised once from methylene chloride/ether. M.p. 119°–120°.

EXAMPLE 2

In a manner analogous to that described in Example 1, there is obtained:
4-chloro-5-cyano-N-[2-[4-(p-fluorobenzoyl)-piperidinyl]-ethyl]-2-methoxybenzamide methanesulphonate, m.p. 178°–180°, using, as starting materials, 41.4 g (0.2 mol) of 4-(p-fluorobenzoyl)-piperidine and 31.8 g (0.1 mol) of N-(2-bromoethyl-4-chloro-5-cyano-2-methoxybenzamide in 240 ml of dioxan.

The starting material is manufactured as follows:

10.7 ml (33.6 g; 0.21 mol) of bromine are added dropwise, while stirring at room temperature, to a solution of 37.3 g (0.2 mol) of 4-chloro-2-methoxybenzoic acid in 500 ml of glacial acetic acid and 500 ml of water. The whole is then stirred for a further hour, 500 ml of water are then added, the precipitated 5-bromo-4-chloro-2-methoxybenzoic acid is filtered with suction and the filtration residue is subsequently washed with water.

A solution of 26.5 g (0.1 mol) of 5-bromo-4-chloro-2-methoxybenzoic acid in 150 ml of ethanol is saturated with hydrogen chloride gas and then left to stand for 15 hours. Concentration by evaporation in a water-jet vacuum is then carried out and the residue is taken up in methylene chloride and extracted by shaking with sodium bicarbonate. The methylene chloride solution is dried over magnesium sulphate and then concentrated by evaporation in a water-jet vacuum. 5-Bromo-4-chloro-2-methoxybenzoic acid ethyl ester of m.p. 79°–81° remains as residue.

14.7 g (0.05 mol) of 5-bromo-4-chloro-2-methoxybenzoic acid ethyl ester, 5.4 g (0.06 mol) of copper(I) cyanide and 8 ml of dimethylformamide are heated at 190° for three hours while stirring under a nitrogen atmosphere. After cooling, the reaction mixture is stirred well with 250 ml of methylene chloride and 250 ml of 2N hydrochloric acid. The insoluble portions are filtered off with suction and the layers are separated in a separating funnel. The methylene chloride solution is washed neutral with water and then concentrated by evaporation. 4-Chloro-5-cyano-2-methoxybenzoic acid ethyl ester is obtained as residue which, after recrystallisation from methylene chloride/hexane, melts at 102°–103°.

For hydrolysis, 24 g (0.1 mol) of 4-chloro-5-cyano-2-methoxybenzoic acid ethyl ester are stirred for 15 hours in 500 ml of methanol, 100 ml of water and 110 ml of 1N sodium hydroxide solution. The methanol is then drawn off in a water-jet vacuum, and 4-chloro-5-cyano-2-methoxybenzoic acid is precipitated from the remaining solution by the addition of dilute hydrochloric acid. The precipitate is filtered with suction and then recrystallised from dioxan. 4-Chloro-5-cyano-2-methoxybenzoic acid of melting point 191°–192° is obtained.

In a manner analogous to that described in Example 3, there is obtained:
4-chloro-5-cyano-2-methoxybenzoic acid chloride using, as starting materials, 8.5 g (0.04 mol) of 4-chloro-5-cyano-2-methoxybenzoic acid and 12 ml (19 g; 0.16 mol) of thionyl chloride in 120 ml of chloroform.

In a manner analogous to that described in Example 1, there is obtained:
N-(2-bromoethyl)-4-chloro-5-cyano-2-methoxybenzamide of melting point 127°–129° using, as starting materials, 23 g (0.1 mol) of 4-chloro-5-cyano-2-methoxybenzoic acid chloride, 20.5 g (0.1 mol) of 2-bromoethylamine hydrobromide and 27.1 g (0.21 mol) of ethyldiisopropylamine.

EXAMPLE 3

In a manner analogous to that described in Example 1, there is obtained:
5-bromo-4-chloro-N-[2-[4-(p-fluorobenzoyl)-piperidinyl]-ethyl]-2-methoxybenzamide of melting point 166°–168° using, as starting materials, 43.5 g (0.21 mol) of p-fluorobenzoylpiperidine and 37.1 g (0.1 mol) of N-(2-bromoethyl)-5-bromo-4-chloro-2-methoxybenzamide in 200 ml of dioxan.

The starting material is manufactured as follows:

13.3 g (0.05 mol) of 5-bromo-4-chloro-2-methoxybenzoic acid in 10 ml of chloroform and 6.6 ml (10.7 g; 0.09 mol) of thionyl chloride are boiled for 2 hours. The reaction mixture is then concentrated by evaporation in a rotary evaporator, with 5-bromo-4-chloro-2-methoxybenzoic acid chloride remaining behind in the form of white powder.

In a manner analogous to that described in Example 1, there is obtained:
N-(2-bromoethyl)-5-bromo-4-chloro-2-methoxybenzamide of melting point 99°–100° using, as starting materials, 5.7 g (0.02 mol) of 5-bromo-4-chloro-2-methoxybenzoic acid chloride, 4.1 g (0.02 mol) of 2-bromoethylamine hydrobromide and 5.2 g (0.04

EXAMPLE 4

In a manner analogous to that described in Example 1, there is obtained:
N-[2-[4-(p-fluorobenzoyl)-piperidinyl]-ethyl]-4-fluoro-2-methoxybenzamide hydrochloride, m.p. 211° with decomposition, using, as starting materials, 41.4 g (0.2 mol) of 4-(p-fluorobenzoyl)-piperidine and 27.6 g (0.1 mol) of N-(2-bromoethyl)-4-fluoro-2-methoxybenzamide in 120 ml of dioxan.

The starting material N-(2-bromoethyl)-4-fluoro-2-methoxybenzamide of melting point 92°–94° is manufactured analogously to Example 1 using, as starting materials, 18.9 g (0.1 mol) of 4-fluoro-2-methoxybenzoic acid chloride (manufactured according to U.S. Pat. No. 3,177,252), 20.5 g (0.1 mol) of 2-bromoethylamine hydrobromide and 27.1 g (0.21 mol) of ethyldiisopropylamine.

EXAMPLE 5

In a manner analogous to that described in Example 1, there is obtained:
5-bromo-N-[2-(4-(p-fluorobenzoyl)-piperidinyl]-ethyl]-4-fluoro-2-methoxybenzamide of melting point 152°–153° using, as starting materials, 45.5 g (0.22 mol) of 4-(p-fluorobenzoyl)-piperidine and 35.5 g (0.1 mol) of N-(2-bromoethyl)-5-bromo-4-fluoro-2-methoxybenzamide in 200 ml of dioxan.

The starting material is manufactured as follows:

In a manner analogous to that described in Example 2, there is obtained:
5-bromo-4-fluoro-2-methoxybenzoic acid of melting point 176°–178° using, as starting materials, 3.4 g (0.02 mol) of 4-fluoro-2-methoxybenzoic acid, 1.07 ml (3.35 g; 0.21 mol) of bromine in 90 ml of glacial acetic acid and 140 ml of water.

In a manner analogous to that described in Example 3, there is obtained:
5-bromo-4-fluoro-2-methoxybenzoic acid chloride in the form of white powder using, as starting materials, 5.0 g (0.02 mol) of 5-bromo-4-fluoro-2-methoxybenzoic acid, 4.3 ml (7.1 g; 0.06 mol) of thionyl chloride and 15 ml of chloroform.

In a manner analogous to that described in Example 1, there is obtained:
N-(2-bromoethyl)-5-bromo-4-fluoro-2-methoxybenzamide of melting point 91°–95° using, as starting materials, 5.4 g (0.02 mol) of 5-bromo-4-fluoro-2-methoxybenzoic acid chloride, 4.1 g (0.02 mol) of 2-bromoethylamine hydrobromide and 5.2 g (0.04 mol) of ethyldiisopropylamine in 30 ml of methylene chloride.

EXAMPLE 6

N-[2-[4-(p-fluorobenzoyl)-piperidinyl]-ethyl]-2-methoxy-5-trifluoromethylbenzamide hydrochloride, m.p. 212° with decomposition, using, as starting materials, 41.4 g (0.2 mol) of 4-(p-fluorobenzoyl)piperidine and 32.6 g (0.1 mol) of N-(2-bromoethyl)-2-methoxy-5-trifluoromethylbenzamide in 180 ml of dioxan.

The starting material N-(2-bromoethyl)-2-methoxy-5-trifluoromethylbenzamide of melting point 85°–86° is manufactured analogously to Example 1 using, as starting materials, 23.9 g (0.1 mol) of 2-methoxy-5-trifluoromethylbenzoic acid chloride (manufactured according to French Pat. No. 1,472,025), 20.5 g (0.1 mol) of 2-bromoethylamine hydrobromide and 27.1 g (0.21 mol) of ethyldiisopropylamine.

EXAMPLE 7

In a manner analogous to that described in Example 1, there is obtained:
2-methoxy-5-sulphamoyl-N-[2-[4-(p-fluorobenzoyl)-piperidinyl]-ethyl]-benzamide of melting point 183°–185° using, as starting materials, 45.5 g (0.22 mol) of 4-(p-fluorobenzoyl)-piperidine and 33.7 g (0.1 mol) of N-(2-bromoethyl)-2-methoxy-5-sulphamoylbenzamide in 250 ml of dimethylformamide.

The starting material N-(2-bromoethyl)-2-methoxy-5-sulphamoylbenzamide of melting point 179° with decomposition is manufactured analogously to Example 1 using, as starting material, 26.5 g (0.1 mol) of 2-methoxy-5-sulphamoylbenzoic acid chloride (manufactured according to French Pat. No. 1,472,025), 20.5 g of 2-bromoethylamine hydrobromide and 21.2 g (0.21 mol) of triethylamine.

EXAMPLE 8

24.1 g (0.1 mol) of 2-(5-chloro-2-methoxy-4-methylaminophenyl)-2-oxazoline, 22.8 g (0.11 mol) of 4-(p-fluorobenzoyl)-piperidine and 120 ml of dioxan are boiled under a nitrogen atmosphere for 18 hours. The resulting dark brown solution is concentrated by evaporation in a water-jet vacuum. A viscous oil is obtained which is dissolved in 300 ml of acetone, and, while stirring, an ethereal hydrogen chloride solution is added thereto until a Congo-acid reaction is obtained, the product beginning to crystallise. The precipitated 5-chloro-N-[2-[4-(p-fluorobenzoyl)piperidinyl]-ethyl]-2-methoxy-4-methylaminobenzamide hydrochloride is filtered with suction. It melts at 230° with decomposition.

The starting material is manufactured as follows:

11.2 g (0.11 mol) of triethylamine are added dropwise, while stirring under a nitrogen atmosphere, to a solution of 21.6 g (0.1 mol) of 5-chloro-2-methoxy-4-methylaminobenzoic acid (manufactured according to S. Iwanami et al., J. Med. Chem. 1981, (24), 1224) in 250 ml of methylene chloride. There is then added to the resulting solution, at $-10°$, 10.9 g (0.1 mol) of chloroformic acid ethyl ester. The whole is stirred at that temperature for a further 30 minutes with 20.5 g (0.1 mol) of 2-bromoethylamine hydrobromide and 10.1 g (0.1 mol) of triethylamine. The cooling bath is then removed and the reaction mixture is stirred at room temperature for 4 hours. For working up, 1 liter of methylene chloride and 1 liter of water are added, the aqueous phase is adjusted to pH 5 with 2N hydrochloric acid and the layers are separated in a separating funnel. Sodium bicarbonate is added to the aqueous phase and extraction is then carried out with methylene chloride. After concentrating the methylene chloride by evaporation, 2-(5-chloro-2-methoxy-4-methylaminophenyl)-2-oxazoline of melting point 159°–161° is obtained.

EXAMPLE 9

In a manner analogous to that described in Example 8, there is obtained:
N-[2-[4-(p-fluorobenzoyl)-piperidinyl]-ethyl]-2-methoxy-5-dimethylsulphamoylbenzamide hydrochloride of melting point 172° with decomposition using, as starting materials, 28.4 g (0.1 mol) of 2-(5-dimethylsulphamoyl-2-methoxyphenyl)-2-oxazoline and 20.7 g (0.1 mol) of 4-(p-fluorobenzoyl)-piperidine and 140 ml of dioxan.

The starting material 2-(5-dimethylsulphamoyl-2-methoxyphenyl)-2-oxazoline of melting point 135°–138° is manufactured analogously to Example 8 using, as starting materials, 24.3 g (0.1 mol) of 5-dimethylsulphamoyl-2-methoxybenzoic acid, 21.3 g (0.21 mol) of triethylamine, 10.9 g (0.1 mol) of chloroformic acid ethyl ester and 20.5 g (0.1 mol) of 2-bromoethylamine hydrobromide.

EXAMPLE 10

20.2 g (0.1 mol) of N-(5-cyano-2-methoxybenzoyl)aziridine, 22.8 g (0.11 mol) of 4-(p-fluorobenzoyl)-piperidine and 250 ml of toluene are heated, while stirring, at 80° for 5 hours. After cooling, the precipitated 5-cyano-N-[2-[4-(p-fluorobenzoyl)piperidinyl]-ethyl]-2-methoxybenzamide is filtered with suction and then washed with a small amount of toluene. M.p. 167°–169°.

The starting material is manufactured as follows:

A solution of 9.8 g (0.05 mol) of 5-cyano-2-methoxybenzoyl chloride in 50 ml of methylene chloride is added dropwise, while stirring well at a reaction temperature of 3°–5°, to a mixture of 100 ml of 0.5N sodium hydroxide solution and 2.3 g (0.53 mol) of aziridine in 30 ml of toluene, and the reaction mixture is then stirred at 5° for a further hour. The layers are then separated in a separating funnel, and the organic phase is extracted by shaking with 50 ml of water, dried over magnesium sulphate and concentrated by evaporation in a water-jet vacuum. N-(5-cyano-2-methoxybenzoyl)-aziridine of melting point 99°–101° remains as residue.

EXAMPLE 11

In a manner analogous to that described in Example 8, there is obtained:
3-bromo-N-[2-[4-(p-fluorobenzoyl)-piperidinyl]ethyl]-4-methoxybenzamide methanesulphonate of melting point 125° using, as starting materials, 25.6 g (0.1 mol) of 2-(3-bromo-4-methoxyphenyl)-2-oxazoline and 20.7 g (0.1 mol) of 4-(p-fluorobenzoyl)piperidine in 75 ml of toluene.

The starting material 2-(3-bromo-4-methoxyphenyl)-2-oxazoline of melting point 95° is manufactured analogously to Example 8 using, as starting materials, 15.2 g (0.1 mol) of 3-bromo-4-methoxybenzoic acid, 21.3 g (0.21 mol) of triethylamine, 10.9 g (0.1 mol) of chloroformic acid ethyl ester and 20.5 g (0.1 mol) of 2-bromoethylamine hydrobromide.

EXAMPLE 12

In a manner analagous to that described in Example 8, there is obtained:
N-[2-[4-(p-fluorobenzoyl)-piperidinyl]-ethyl]-2-methoxybenzamide hydrochloride of melting point 205° with decomposition using, as starting materials, 17.7 g (0.1 mol) of 2-(2-methoxyphenyl)-2-oxazoline and 10.7 g (0.1 mol) of 4-(p-fluorobenzoyl)-piperidine and 40 ml of dioxan.

The starting material 2-(2-methoxyphenyl)-2-oxazoline of melting point 35°–38° is manufactured analogously to Example 8 using, as starting materials, 15.2 g (0.1 mol) of 2-methoxybenzoic acid, 21.3 g (0.21 mol) of triethylamine, 10.9 g (0.1 mol) of chloroformic acid ethyl ester and 20.5 g (0.1 mol) of 2-bromoethylamine hydrobromide.

EXAMPLE 13

0.38 g (0.01 mol) of sodium borohydride are added, while stirring, to a suspension of 4.1 g (0.01 mol) of 5-cyano-N-[2-[4-(p-fluorobenzoyl)-piperidinyl]ethyl]-2-methoxybenzamide in 50 ml of ethanol and the whole is stirred for 1 hour at room temperature. There is added to the resulting clear solution 1 ml of acetone and the whole is then concentrated in a water-jet vacuum. The residue is taken up in methylene chloride and water, the layers are separated in a separating funnel and, after being dried over magnesium sulphate, the organic phase is concentrated by evaporation. 5-Cyano-N-[2-[4-[(4-fluorophenyl)hydroxymethylene]-piperidinyl]-ethyl]-2-methoxybenzamide of melting point 135°–137° is obtained as residue.

EXAMPLE 14

45 g (0.35 mol) of ethyldiisopropylamine are added dropwise, while stirring at from −10° to 0° under a nitrogen atmosphere, to a mixture of 32.3 g (0.1 mol) of N-(2-aminoethyl)-4-(p-fluorobenzoyl)-piperidine hydrochloride and 24 g of 3-bromo-4-fluorobenzoyl chloride in 250 ml of methylene chloride. The reaction mixture is then heated to room temperature and is maintained at that temperature for 4 hours. 200 ml of 1N sodium hydroxide solution are then added, the layers are separated, and the organic phase is washed neutral with water, dried over magnesium sulphate and concentrated in a water-jet vacuum. 3-Bromo-4-fluoro-N-[2-[4-(p-fluorobenzoyl)-piperidinyl]-ethyl]-benzamide of melting point 135° remains as residue.

To convert it into the hydrochloride, this base is dissolved in methylene chloride and ethereal hydrogen chloride solution is added thereto. The hydrochloride melts at 189°–190°.

The N-(2-aminoethyl)-4-(p-fluorobenzoyl)piperidine hydrochloride used as starting material is manufactured as follows:

29.5 g (0.23 mol) of ethyldiisopropylamine are added, while stirring, to a suspension of 24.4 g (0.1 mol) of 4-(p-fluorobenzoyl)-piperidine hydrochloride and 8.3 g (0.11 mol) of chloroacetonitrile in 50 ml of methylene chloride. The reaction mixture is stirred at room temperature for 15 hours. 150 ml of ether are then added and extraction is carried out by shaking with 2N hydrochloric acid. This acid extract is rendered alkaline with 2N sodium hydroxide solution and the base which separates is extracted by shaking with a 3:1 ether/methylene chloride mixture. The product is washed neutral, dried over magnesium sulphate and concentrated by evaporation. N-(cyanomethyl)-4-(p-fluorobenzoyl)-piperidine of melting point 133°–134° remains as residue.

14.1 g (0.05 mol) of N-(cyanomethyl)-4-(p-fluorobenzoyl)-piperidine are dissolved in 1.5 liters of glacial acetic acid and 30 ml of concentrated hydrochloric acid and hydrogenated together with 2 g of platinum oxide in a hydrogen atmosphere. After 6 hours, the theoretical amount of 2.25 liters of hydrogen is absorbed. The catalyst is then filtered off with suction and the filtrate is concentrated to approximately 30 ml in a water-jet vacuum. There is added to the resulting crystal mass 5 ml of isopropanol and 15 ml of ether and filtration with suction is carried out. After filtration with suction and drying, N-(2-aminoethyl)-4-(p-fluorobenzoyl)-piperidine hydrochloride is obtained which, after recrystallisation from methanol, melts at 265° with decomposition.

The 3-bromo-4-fluorobenzoyl chloride used as starting material is manufactured analogously to Example 3 from 21.9 g (0.1 mol) of 3-bromo-4-fluorobenzoic acid (manufactured according to J. Indian Chem. Soc. 21, 115 (1944)) and 10 ml of thionyl chloride.

EXAMPLE 15

In a manner analogous to that described in Example 14, there are obtained:

2-bromo-4-fluoro-N-[2-[4-(p-fluorobenzoyl)-piperidinyl]-ethyl]-benzamide of melting point 123°–125° using, as starting materials, 3.23 g (0.01 mol) of N-(2-aminoethyl)-4-(p-fluorobenzoyl)-piperidine hydrochloride, 2.6 g (0.01 mol) of 2-bromo-4-fluorobenzoyl chloride and 4.5 g (0.035 mol) of ethyldiisopropylamine in 25 ml of methylene chloride; and N-[2-[4-(p-fluorobenzoyl)-piperidinyl]-ethyl]-2,6-dimethoxybenzamide hydrochloride of melting point 232°–234° with decomposition using, as starting materials, 32.3 g (0.1 mol) of N-(2-aminoethyl)-4-(p-fluorobenzoyl)-piperidine hydrochloride, 20 g of 2,6-dimethoxybenzoyl chloride and 45 g (0.35 mol) of ethyldiisopropylamine in 200 ml of methylene chloride.

EXAMPLE 16

In a manner analogous to that described in Example 1, there is obtained:

4-fluoro-N-[2-[4-(p-fluorobenzoyl)-piperidinyl]ethyl]-benzamide hydrochloride, m.p. 240°–242°, using, as starting materials, 6.2 g (0.03 mol) of 4-(p-fluorobenzoyl)-piperidine and 7.4 g (0.03 mol) of N-(2-bromoethyl)-4-fluorobenzamide in 25 ml of dimethylformamide.

EXAMPLE 17

In a manner analogous to that described in Example 10, there is obtained:

5-bromo-N-[2-[4-(p-fluorobenzoyl)-piperidinyl]ethyl]-2-methoxybenzamide hydrochloride of melting point 213° with decomposition using, as starting materials, 5.2 g (0.02 mol) of N-(5-bromo-2-methoxybenzoyl)-aziridine and 4.4 g (0.021 mol) of 4-(p-fluorobenzoyl)-piperidine in 16 ml of toluene.

The starting material N-(5-bromo-2-methoxybenzoyl)-aziridine is manufactured analogously to Example 10 using, as starting materials, 9 g (0.21 mol) of aziridine, 27.1 g (0.21 mol) of ethyldiisopropylamine and 50 g (0.02 mol) of 5-bromo-2-methoxybenzoyl chloride in 300 ml of methylene chloride.

There is also obtained in a manner analogous to that described in Example 10:

3-cyano-N-[2-[4-(p-fluorobenzoyl)-piperidinyl]ethyl]-4-methoxybenzamide hydrochloride of melting point 230° with decomposition using, as starting materials, 20.2 g (0.1 mol) of N-(3-cyano-4-methoxybenzoyl)-aziridine and 22.8 g (0.11 mol) of 4-(p-fluorobenzoyl)-piperidine in 120 ml of toluene.

The starting material N-(3-cyano-4-methoxybenzoyl)-aziridine of melting point 176°–177° is manufactured using, as starting materials, 4.52 g (0.105 mol) of aziridine, 12.9 g (0.1 mol) of ethyldiisopropylamine and 19.6 g (0.1 mol) of 3-cyano-4-methoxybenzoyl chloride in 150 ml of methylene chloride.

EXAMPLE 18

In a manner analogous to that described in Example 14, there are obtained:

3,5-dichloro-N-[2-[4-(p-fluorobenzoyl)-piperidinyl]ethyl]-2-methoxy-4-methylbenzamide methanesulphonate of melting point 112°–114° using, as starting materials, 3.23 g (0.01 mol) of N-(2-aminoethyl)-4-(p-fluorobenzoyl)-piperidine hydrochloride, 2.54 g (0.01 mol) of 3,5-dichloro-2-methoxy-4-methylbenzoyl chloride and 4.5 g (0.035 mol) of ethyldiisopropylamine in 25 ml of methylene chloride;

N-[2-[4-(p-fluorobenzoyl)-piperidinyl]-ethyl]-2-methoxy-5-methylmercaptobenzamide hydrochloride of melting point 209° with decomposition using, as starting materials, 3.23 g (0.01 mol) of N-(2-aminoethyl)-4-(p-fluorobenzoyl)-piperidine hydrochloride, 2.17 g (0.01 mol) of 2-methoxy-5-methylmercaptobenzoyl chloride and 4.5 g (0.035 mol) of ethyldiisopropylamine in 30 ml of methylene chloride; and N-[2-[4-(p-fluorobenzoyl)-piperidinyl]-ethyl]-2-methoxy-5-methanesulphonylbenzamide hydrochloride of melting point 163°–164° using, as starting materials, 6.5 g (0.02 mol) of N-(2-aminoethyl)-4-(p-fluorobenzoyl)-piperidine hydrochloride, 4.99 g (0.02 mol) of 2-methoxy-5-methanesulphonylbenzoyl chloride and 9 g (0.07 mol) of ethyldiisopropylamine in 50 ml of methylene chloride.

EXAMPLE 19

In a manner analogous to that described in Example 14, there is obtained:

5-cyano-N-[2-[4-(p-fluorobenzyl)-piperidinyl]ethyl]-2-methoxybenzamide hydrochloride of melting point 147°–148° using, as starting materials, 4.6 g (0.015 mol) of N-(2-aminoethyl)-4-(p-fluorobenzyl)-piperidine dihydrochloride, 2.93 g (0.015 mol) of 5-cyano-2-methoxybenzoyl chloride and 6.4 g (0.05 mol) of ethyldiisopropylamine in 35 ml of methylene chloride.

The N-(2-aminoethyl)-4-(p-fluorobenzyl)-piperidine dihydrochloride used as starting material is manufactured as follows:

24.4 g (0.10 mol) of 4-(p-fluorobenozyl)-piperidine hydrochloride are hydrogenated at 70° in 120 ml of trifluoroacetic acid with 5 g of palladiumon-carbon (5 %) until the theoretical amount of hydrogen has been absorbed. The catalyst is then filtered off with suction and the filtrate is concentrated by evaporation in a water-jet vacuum. The residue is dissolved in 150 ml of water, 50 ml of concentrated sodium hydroxide solution are added and extraction is then carried out with 250 ml of ether. The ethereal solution so obtained is rendered weakly Congo-acidic with hydrogen chloride gas, with 4-(p-fluorobenzyl)-piperidine hydrochloride being precipitated. M.p. 166°–166.5°.

28.4 g (0.22 mol) of ethyldiisopropylamine are added dropwise, while stirring, to a suspension of 23 g (0.10 mol) of 4-(p-fluorobenzyl)-piperidine hydrochloride and 8.3 g (0.11 mol) of chloroacetonitrile in 75 ml of methylene chloride. The reaction mixture is stirred at room temperature for 15 hours. 150 ml of ether are then added and extraction is carried out by shaking with 2N hydrochloric acid. This acid extract is rendered alkaline with 2N sodium hydroxide solution and the base which separates is extracted by shaking with methylene chloride. The product is washed neutral with water, dried over sodium sulphate and concentrated by evaporation. The residue is dissolved in a small amount of isopropanol and rendered weakly Congo-acidic with ethereal hydrogen chloride solution, with N-(cyanomethyl)-4-

(p-fluorobenzyl)-piperidine hydrochloride being precipitated. M.p. 158°–160°.

13.44 g (0.05 mol) of N-(cyanomethyl)-4-(p-fluorobenzyl)-piperidine hydrochloride are dissolved in 300 ml of glacial acetic acid and 7 ml of concentrated hydrochloric acid and hydrogenated together with 1 g of platinum oxide in a hydrogen atmosphere. After 4 hours, the theoretical amount of 2.25 liters of hydrogen is absorbed. The catalyst is then filtered off with suction and the filtrate is concentrated to approximately 30 ml in a water-jet vacuum. There is then added to the resulting crystal mass 5 ml of isopropanol and 10 ml of ether and filtration with suction is carried out. There is thus obtained N-(2-aminoethyl)-4-(p-fluorobenzyl)-piperidine dihydrochloride which, after recrystallisation from ethanol/ether, melts at 171°–173°.

EXAMPLE 20

6.69 g (0.015 mol) of 5-cyano-N-[2-[4-(p-fluorobenzoyl)-piperidinyl]-ethyl]-2-methoxybenzamide hydrochloride are suspended in 50 ml of methanol and 50 ml of toluene. While stirring and cooling, hydrogen chloride gas is introduced at 0° until a clear solution is obtained. 100 ml of ice-water are then poured in slowly and the whole is then heated at 70° for a further hour. After cooling, the reaction mixture is carefully rendered weakly alkaline with potash and the resulting mixture is extracted with methylene chloride. This methylene chloride solution is washed neutral with water, dried over magnesium sulphate and concentrated by evaporation in a water-jet vacuum. The residue, N-[2-[4-(p-fluorobenzoyl)-piperidinyl]-ethyl]-2-methoxy-5-methoxycarbonylbenzamide, is dissolved in methylene chloride/ether 1:4 and converted into the hydrochloride with ethereal hydrogen chloride solution. The hydrochloride is filtered off with suction and recrystallised once from methylene chloride/acetone. M.p. 221° with decomposition.

EXAMPLE 21

6.69 g (0.015 mol) of 5-cyano-N-[2-[4-(p-fluorobenzoyl)-piperidinyl]-ethyl]-2-methoxybenzamide hydrochloride are dissolved under a nitrogen atmosphere in 60 ml of 85% sulphuric acid and the whole is left to stand at room temperature for 7 days. This solution is then added dropwise, while stirring, to a mixture of 130 ml of concentrated ammonia and 200 g of ice, a white precipitate being formed. The latter is filtered off with suction and recrystallised from methylene chloride/methanol. There is thus obtained 5-carbamoyl-N-[2-[4-(p-fluorobenzoyl)-piperidinyl]-ethyl]-2-methoxybenzamide of melting point 236°–238°.

To convert it into the hydrochloride, the free base is suspended in methylene chloride and ethereal hydrogen chloride solution is added thereto, while stirring, until a Congo-acid reaction is obtained, a clear solution being formed. Ether is then added until crystallisation begins. There is thus obtained 5-carbamoyl-N-[2-[4-(p-fluorobenzoyl)-piperidinyl]-ethyl]-2-methoxybenzamide hydrochloride of melting point 240° with decomposition.

EXAMPLE 22

2.14 g (0.01 mol) of 2-methoxy-5-methanesulphinylbenzoic acid and 3.23 g (0.01 mol) of N-(2-aminoethyl)-4-(p-fluorobenzoyl)-piperidine dihydrochloride are dissolved in 10 ml of dimethylformamide, and 2.13 g (0.021 mol) of triethylamine are added. While stirring under a nitrogen atmosphere, 3.26 g (0.0105 mol) of triphenyl phosphite are added and the resulting reaction mixture is heated at 85°–90° for 2.5 hours. After cooling, ethereal hydrogen chloride solution is added until a Congo-acid reaction is obtained and the ethereal solution which has separated is then decanted. Methylene chloride and potassium carbonate solution are added to the residue, the layers are separated, and the methylene chloride solution is dried over potash and concentrated. The residue, N-[2-[4-(p-fluorobenzoyl)-piperidinyl]-ethyl]-2-methoxy-5-methanesulphinylbenzamide, is converted into the hydrochloride in methylene chloride/methanol with ethereal hydrogen chloride solution. The hydrochloride is precipitated by the addition of ether. There is thus obtained N-[2-[4-(p-fluorobenzoyl)-piperidinyl]-ethyl]-2-methoxy-5-methanesulphinylbenzamide hydrochloride which, after recrystallisation once from methylene chloride/methanol, melts at 194° with decomposition.

EXAMPLE 23

In a manner analogous to that described in Example 10, there are obtained:

5-cyano-2-methoxy-N-[2-[4-(2-thenoyl)-piperidinyl]-ethyl]-benzamide hydrochloride of melting point 168° with decomposition using, as starting materials, 4.04 g (0.02 mol) of N-(5-cyano-2-methoxybenzoyl)-aziridine and 3.9 g (0.02 mol) of 4-(2-thenoyl)-piperidine in 22 ml of toluene;

p-fluoro-N-[2-[4-(2-thenoyl)-piperidinyl]-ethyl]benzamide hydrochloride of melting point 204°–205° using, as starting materials, 4.95 g (0.03 mol) of p-fluorobenzoylaziridine and 5.85 g (0.03 mol) of 4-(2-thenoyl)-piperidine in 25 ml of toluene;

N-[2-[4-(p-chlorobenzoyl)-piperidinyl]-ethyl]-5-cyano-2-methoxybenzamide methanesulphonate of melting point 177°–178° using, as starting materials, 4.04 g (0.02 mol) of N-(5-cyano-2-methoxybenzoyl)-aziridine and 4.46 g (0.02 mol) of 4-(p-chlorobenzoyl)-piperidine in 20 ml of toluene; and N-[2-[4-(p-chlorobenzoyl)-piperidinyl]-ethyl]-p-fluorobenzamide methanesulphonate of melting point 149°–151° using, as starting materials, 3.3 g (0.02 mol) of p-fluorobenzoylaziridine and 4.46 g (0.02 mol) of 4-(p-chlorobenzoyl)-piperidine in 20 ml of toluene.

EXAMPLE 24

In a manner analogous to that described in Example 10, there is obtained: p-fluoro-N-[3-[4-(p-fluorobenzoyl)-piperidinyl]-2-methylpropyl]-benzamide hydrochloride of melting point 238°–240° using, as starting materials, 1.93 g (0.01 mol) of N-(p-fluorobenzoyl)-2,2-dimethylaziridine and 2.07 g (0.01 mol) of 4-(p-fluorobenzoyl)-piperidine in 10 ml of toluene.

The N-(p-fluorobenzoyl)-2,2-dimethylaziridine used as starting material is obtained analogously to Example 10, in the form of a viscous oil using, as starting materials, 2.13 g (0.03 mol) of 2,2-dimethylaziridine and 4.76 g (0.03 mol) of p-fluorobenzoyl chloride in 30.6 ml of 1N sodium hydroxide solution.

EXAMPLE 25

26.8 g (0.11 mol) of 4-(p-fluorobenzoyl)-piperidine hydrochloride 34.5 g (0.25 mol) of potash and 25.3 g (0.1 mol) of N-(3-chloropropyl)-5-cyano-2-methoxybenzamide are boiled together with 0.5 g of potassium iodide in 250 ml of ethanol, while stirring for 15 hours. The reaction mixture is then concentrated by evaporation in a water-jet vacuum and the residue is taken up in ether, a small amount of methylene chloride and water. After separating off the aqueous phase, the basic portions are separated from the organic phase by extraction by shaking with 2N methanesulphonic acid. The acid extracts are adjusted to pH 9 with sodium hydroxide solution and then extracted with methylene chloride. The methylene chloride solution is washed neutral with water, dried over magnesium sulphate and concentrated by evaporation in a water-jet vacuum. The resulting crude product is subjected to flash-chromatography, the chloroform/methanol 49:1 fractions eluting the desired 5-cyano-N-[3-[4-(p-fluorobenzoyl)-piperidinyl]-propyl]-2-methoxybenzamide of melting point 133°–135°.

To convert it into the hydrochloride, the free base is dissolved in methylene chloride and an ethereal hydrogen chloride solution is added thereto until a Congo-acid reaction is obtained. Ether is then added until crystallisation begins. There is thus obtained 5-cyano-N-[3-[4-(p-fluorobenzoyl)-piperidinyl]-propyl]-2-methoxybenzamide of melting point 171° with decomposition.

EXAMPLE 26

20.8 g (0.1 mol) of 2-(2,6-dimethoxypyridinyl)-2-oxazoline, 22.8 g (0.11 mol) of 4-(p-fluorobenzoyl)-piperidine, 12.9 g (0.1 mol) of ethyldiisopropylamine and 120 ml of dioxan are heated, while stirring, at 80° for 16 hours. Methylene chloride and water are then added and the pH value is adjusted to pH 9 with saturated potassium carbonate solution. The layers are separated in a separating funnel and the organic phase is concentrated by evaporation in a water-jet vacuum. The resulting residue is dissolved in 150 ml of methanol and, while stirring, water is added, with N-[2-[4-(p-fluorobenzoyl)-piperidinyl]-ethyl]-2,6-dimethoxynicotinic acid amide being precipitated. M.p. 116°–119°.

To convert it into the methanesulphonate, the free base is dissolved in a small amount of methylene chloride and an ethereal methanesulphonic acid solution is then added thereto, while stirring, until a weakly Congo-acid reaction is obtained, with N-[2-[4-(1-fluorobenzoyl)-piperidinyl]-ethyl]-2,6-nicotinic acid amide methanesulphonate being precipitated. The crude product is recrystallised once from isopropanol. M.p. 170°–172°.

The starting material is manufactured as follows:

110.6 g (0.8 mol) of potassium carbonate are dissolved in 120 ml of water and the solution is cooled to 10°. There is then added a mixture of 150 ml of ether and 100 ml of methylene chloride followed by 49.2 g (0.24 mol) of 2-bromoethylamine hydrobromide, and a solution of 40.3 g (0.2 mol) of 2,6-dimethoxynicotinic acid chloride in 100 ml of methylene chloride is then rapidly added dropwise at a reaction temperature of 15°–20°. The reaction mixture is then heated to room temperature and is stirred at that temperature for a further hour. 50 ml of water are then added and the layers are separated in a separating funnel. The organic phase is concentrated by evaporation in a water-jet vacuum, with 2-(2,6-dimethoxypyrimidinyl)-2-oxazoline remaining behind in the form of slightly yellowish crystals.

EXAMPLE 27

Tablets each containing 25 mg of active ingredient, for example 5-cyano-N-[2-[4-(p-fluorobenzoyl)-piperidinyl]-ethyl]-2-methoxybenzamide, can be produced in the following manner:

| Constituents (for 1000 tablets) | |
|---|---|
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Production:

All the solid ingredients are first of all pressed through a sieve of 0.6 mm mesh width. The active ingredient, the lactose, the talc, the magnesium stearate and half of the starch are then mixed. The other half of the starch is suspended in 40 ml of water and this suspension is added to a boiling solution of the polyethylene glycol in 100 ml of water. The resulting starch paste is added to the main portion and the mixture is granulated, if necessary with the addition of water. The granulate is dried overnight at 35°, pressed through a sieve of 1.2 mm mesh width and pressed to form tablets of approximately 6 mm diameter which are concave on both sides.

EXAMPLE 28

Tablets each containing 0.02 g of the methanesulphonic acid salt of 5-cyano-N-[2-[4-(p-fluorobenzoyl)-piperidinyl]-ethyl]-2-methoxybenzamide are produced as follows:

| Composition (for 10,000 tablets) | |
|---|---|
| active ingredient | 200.00 g |
| lactose | 290.80 g |
| potato starch | 274.70 g |
| stearic acid | 10.00 g |
| talc | 200.00 g |
| magnesium stearate | 2.50 g |
| colloidal silica | 32.00 g |
| ethanol | q.s. |

A mixture of the active ingredient, the lactose and 194.70 g of the potato starch is moistened with an ethanolic solution of the stearic acid and granulated through a sieve. After drying, the remainder of the potato starch, the talc, the magnesium stearate and the colloidal silica are mixed in and the mixture is pressed to form tablets each weighing 0.1 g which may, if desired, be provided with dividing notches for finer adaptation of the dose.

EXAMPLE 29

Capsules each containing 0.025 g of the active ingredient, for example 5-cyano-N-[2-[4-(p-fluorobenzoyl)-piperidinyl]-ethyl]-2-methoxybenzamide, can be produced as follows:

| Composition (for 1000 capsules) | |
|---|---|
| active ingredient | 25.00 g |
| lactose | 249.00 g |
| gelatine | 2.00 g |
| corn starch | 10.00 g |
| talc | 15.00 g |
| water | q.s. |

The active ingredient is mixed with the lactose, and the mixture is moistened uniformly with an aqueous solution of the gelatine and granulated through a sieve having a mesh width of 1.2–1.5 mm. The granulate is mixed with the dried corn starch and the talc, and portions of 300 mg are introduced into hard gelatine capsules (size 1).

I claim:

1. N-(piperidinyl-alkyl)-carboxamides of the general formula

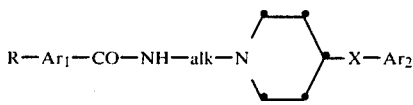

in which
R represents hydroxy, hydroxy etherified by an aliphatic alcohol, or halogen,
$Ar_1$ represents a monocyclic arylene or heteroarylene radical,
alk represents an alkylene group that separates the two N atoms by at least two carbon atoms,
X represents a free or ketalised carbonyl group, free hydroxymethylene or hydroxymethylene esterified by an organic carboxylic acid, or methylene, and
$Ar_2$ represents a monocyclic aryl or heteroaryl radical, and salts thereof, with the proviso that the grouping R—$Ar_1$ is other than a radical of the formula

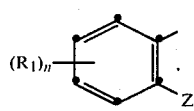

in which $R_1$ is selected from the group consisting of lower alkyl, trifluoromethyl, halogen, lower alkoxy, nitro and cyano and at least one of the radicals $R_1$ represents halogen or lower alkoxy, n represents an integer from 1 to 3, and Z represents nitro, amino, lower alkylamino, arylamino, aryl-lower alkylamino, (thio-)formylamino, (thio-)lower alkanoylamino, (thio-)aroylamino or aryl-(thio-)lower alkanoylamino, if alk and X have the meanings given and $Ar_2$ represents unsubstituted phenyl, thienyl or pyridyl or substituted phenyl having one, two or three substituents selected from the group consisting of halogen, lower alkyl, lower alkoxy, trifluoromethyl and amino.

2. Compounds according to claim 1 of the formula I in which R represents hydroxy, lower alkoxy, lower alkenyloxy or halogen, $Ar_1$ represents a phenylene radical or a monocyclic azaarylene radical having up to and including 3 nitrogen atoms and bonded by a carbon atom, each of which radicals is unsubstituted or mono- or poly-substituted by lower alkyl, lower alkenyl, lower alkadienyl, halo-lower alkyl, hydroxy, lower alkanoyloxy, halogen, lower alkoxy, lower alkenyloxy, halo-lower alkoxy, lower alkanoyl, nitro, cyano, carbamoyl, N-lower alkylcarbamoyl, N,N-di-lower alkylcarbamoyl, carboxy, lower alkoxycarbonyl, amino, N-lower alkylamino, N,N-di-lower alkylamino, sulphamoyl, N-lower alkylsulphamoyl, N,N-di-lower alkylsulphamoyl, lower alkylthio, halo-lower alkylthio, lower alkanesulphinyl, halo-lower alkanesulphinyl, lower alkanesulphonyl and/or by halo-lower alkanesulphonyl, alk represents alkylene that has from 2 up to and including 7 carbon atoms and separates the two N atoms by 2 or 3 carbon atoms, X represents carbonyl, di-lower alkoxymethylene, lower alkylenedioxymethylene, hydroxymethylene, lower alkanoyloxymethylene or methylene and $Ar_2$ represents a phenyl radical or a monocyclic monooxa-, monoaza- or monothia-aryl radical, each of which radicals is unsubstituted or mono- or poly-substituted by lower alkyl, lower alkenyl, lower alkadienyl, halo-lower alkyl, hydroxy, lower alkanoyloxy, halogen, lower alkoxy, lower alkenyloxy, halo-lower alkoxy, lower alkanoyl, nitro, cyano, carbamoyl, N-lower alkylcarbamoyl, N,N-di-lower alkylcarbamoyl, carboxy, lower alkoxycarbonyl, amino, N-lower alkylamino, N,N-di-lower alkylamino, sulphamoyl, N-lower alkylsulphamoyl, N,N-di-lower alkylsulphamoyl, lower alkylthio, halo-lower alkylthio, lower alkanesulphinyl, halo-lower alkanesulphinyl, lower alkanesulphonyl and/or by halo-lower alkanesulphonyl, and salts thereof.

3. Compounds according to claim 1 of the formula I in which R represents lower alkoxy, $Ar_1$ represents phenylene or pyridylene each of which is unsubstituted or mono- or poly-substituted by lower alkyl, halo-lower alkyl, halogen, lower alkoxy, cyano, carbamoyl, amino, N-lower alkylamino, N,N-di-lower alkylamino, sulphamoyl, N,N-di-lower alkylsulphamoyl, halo-lower alkylthio, lower alkanesulphonyl and/or by halo-lower alkanesulphonyl, alk represents alkylene that has from 2 up to and including 3 carbon atoms, X represents carbonyl, hydroxymethylene or methylene and $Ar_2$ represents phenyl substituted by halogen, or unsubstituted thienyl, and salts thereof.

4. Compounds according to claim 1 of the formula I in which, on the one hand, R represents lower alkoxy or halogen and $Ar_1$ represents phenylene which is unsubstituted or mono- or poly-substituted by lower alkyl, halo-lower alkyl, hydroxy, halogen, lower alkoxy, cyano, carbamoyl, lower alkoxycarbonyl, amino, lower alkylamino, di-lower alkylamino, sulphamoyl, N,N-di-lower alkylsulphamoyl, lower alkylthio, lower alkanesulphinyl and/or by lower alkanesulphonyl, or in which, on the other hand, R represents lower alkoxy and $Ar_1$ represents pyridylene which is unsubstituted or substituted by lower alkoxy, and in each case alk represents alkylene that has from 2 up to and including 7 carbon atoms and separates the two N atoms by 2 or 3 carbon atoms, X represents carbonyl, hydroxymethylene or methylene and $Ar_2$ represents phenyl substituted by halogen, or unsubstituted thienyl, and salts thereof.

5. Compounds according to claim 1 of the formula I in which R in each case represents lower alkoxy, $Ar_1$ represents, on the one hand, a phenyl radical which is unsubstituted or mono- or poly-substituted by halo-lower alkyl, halogen, lower alkoxy, cyano, carbamoyl, N-lower alkylamino, sulphamoyl, N,N-di-lower alkylsulphamoyl, halo-lower alkylthio and/or by halo-lower alkanesulphonyl, or, on the other hand, a pyridylene radical which is mono- or poly-substituted by lower alkoxy and/or halogen, alk represents ethylene or 1,3-propylene, X represents carbonyl, hydroxymethylene or methylene and $Ar_2$ represents a phenyl radical substituted by halogen, and salts thereof.

6. Compounds according to claim 1 of the formula I in which the grouping R—$Ar_1$ represents the structural element of the formula

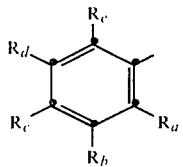

(Ib)

in which one of the radicals $R_a$ and $R_c$ represents the radical R which represents lower alkoxy or halogen and the other represents hydrogen, lower alkyl, halogen or lower alkylamino, and each of the radicals $R_b$, $R_d$ and $R_e$, independently of the others, represents hydrogen, lower alkyl, halo-lower alkyl, hydroxy, halogen, lower alkoxy, cyano, carbamoyl, lower alkoxycarbonyl, amino, sulphamoyl, N,N-di-lower alkylsulphamoyl, lower alkylthio, lower alkanesulphinyl and/or lower alkanesulphonyl, and in which alk represents alkylene that has from 2 up to and including 4 carbon atoms and separates the two N atoms by 2 or 3 carbon atoms, X represents carbonyl, hydroxymethylene or methylene and $Ar_2$ represents phenyl substituted by halogen, or unsubstituted thienyl, and salts thereof.

7. Compounds acording to claim 1 of the formula I in which the grouping R—$Ar_1$ represents the structural element of the formula Ib in which, on the one hand, the radical $R_a$ represents the radical R which represents lower alkoxy having up to and including 4 carbon atoms and $R_c$ represents hydrogen, halogen having an atomic number of up to and including 35 or lower alkylamino having up to and including 4 carbon atoms, or $R_a$ represents hydrogen and $R_c$ represents the radical R which represents lower alkoxy having up to and including 4 carbon atoms, or in which, on the other hand, the radical $R_c$ represents the radical R which represents halogen having an atomic number of up to and including 35 and $R_a$ represents hydrogen or halogen having an atomic number of up to and including 35 and one of the radicals $R_b$ and $R_d$ represents hydrogen, lower alkyl having up to and including 4 carbon atoms, halo-lower alkyl having an atomic number of up to and including 35 and having up to and including 4 carbon atoms, halogen having an atomic number of up to and including 35, lower alkoxy having up to and including 4 carbon atoms, cyano, carbamoyl, lower alkoxycarbonyl having from 2 up to and including 5 carbon atoms, lower alkylthio having up to and including 4 carbon atoms, lower alkanesulphinyl having up to and including 4 carbon atoms or lower alkanesulphonyl having up to and including 4 carbon atoms, and the other and $R_e$ represent hydrogen, and in which in each case alk represents alkylene that has from 2 up to and including 4 carbon atoms and separates the two N atoms by 2 or 3 carbon atoms, X represents carbonyl or hydroxymethylene and $Ar_2$ represents phenyl substituted in the p-position by halogen having an atomic number of up to and including 35, and salts thereof.

8. Compounds according to claim 1 of the formula I in which $Ar_1$ represents, on the one hand, phenylene which is mono- or poly-substituted by halogen having an atomic number of up to and including 35, cyano and/or by N-lower alkylamino having up to and including 4 carbon atoms in the lower alkyl moiety, or, on the other hand, pyridylene, and in each case R represents lower alkoxy having up to and including 4 carbon atoms, alk represents ethylene, X represents carbonyl and $Ar_2$ represents phenyl substituted by halogen having an atomic number of up to and including 35, and salts thereof.

9. Compounds according to claim 1 of the formula I in which the grouping R—$Ar_1$ represents the structural element of the formula Ib in which, on the one hand, $R_a$ represents the radical R which represents lower alkoxy having up to and including 4 carbon atoms, $R_b$ and $R_e$ represent hydrogen, $R_c$ represents lower alkylamino having up to and including 4 carbon atoms and $R_d$ represents halogen having an atomic number of up to and including 35, or $R_c$ represents hydrogen or halogen having an atomic number of up to and including 35 and $R_d$ represents cyano, or in which, on the other hand, $R_a$, $R_d$ and $R_e$ represent hydrogen, $R_b$ represents halogen having an atomic number of up to and including 35 and $R_c$ represents the radical R which represents lower alkoxy having up to and including 4 carbon atoms, and in each case alk represents ethylene, X represents carbonyl or also hydroxymethylene and $Ar_2$ represents 4-fluorophenyl, and salts thereof.

10. Compounds according to claim 1 of the formula I in which the grouping R—$Ar_1$ represents the structural element of the formula Ib in which one of the radicals $R_a$ and $R_b$ represents hydrogen or halogen having an atomic number of up to and including 35, and the other represents hydrogen, $R_c$ represents the radical R which represents halogen having an atomic number of up to and including 35 and each of $R_d$ and $R_e$ represents hydrogen, and alk represents ethylene, X represents carbonyl and $Ar_2$ represents p-fluorophenyl, and salts thereof.

11. Compounds according to claim 1 of the formula I in which the grouping R—$Ar_1$ represents the structural element of the formula Ib in which $R_a$, $R_d$ and $R_e$ represent hydrogen, $R_b$ represents hydrogen or halogen having an atomic number of up to and including 35, and $R_c$ represents the radical R which represents halogen having an atomic number of up to and including 35, alk represents ethylene, X represents carbonyl and $Ar_1$ represents 4-fluorophenyl, and salts thereof.

12. Compounds according to claim 1 of the formula I in which the grouping R—$Ar_1$ represents the structural element of the formula Ib in which $R_a$ represents the radical R which represents lower alkoxy having up to and including 4 carbon atoms, $R_b$, $R_c$ and $R_e$ represent hydrogen and $R_d$ represents cyano, alk represents ethylene, X represents carbonyl and $Ar_2$ represents 4-fluorophenyl, and salts thereof.

13. A compound according to claim 1 of the formula I being 5-cyano-N-[2-[4-(p-fluorobenzoyl)-piperidinyl]-ethyl]-2-methoxy-benzamide or a salt thereof, 4-chloro-5-cyano-N-[2-[4-(p-fluorobenzoyl)-piperidinyl]-ethyl]-2-methoxy-benzamide or a salt thereof, 5-bromo-4-chloro-N-[2-[4-(p-fluorobenzoyl)-piperidinyl]-ethyl]-2-methoxy-benzamide or a salt thereof, N-[2-[4-(p-fluorobenzoyl)-piperidinyl]-ethyl]-4-fluoro-2-methoxy-benzamide or a salt thereof, 5-bromo-N-[2-[4-(p-fluorobenzoyl)-piperidinyl]-ethyl]-4-fluoro-2-methoxy-benzamide or a salt thereof, N-[2-[4-(p-fluorobenzoyl)-piperidinyl]-ethyl]-2-methoxy-5-trifluoromethyl-benzamide or a salt thereof, 2-methoxy-5-sulphamoyl-N-[2-[4-(p-fluorobenzoyl)-piperidinyl]-ethyl]-benzamide or a salt thereof, 5-chloro-N-[2-[4-(p-fluorobenzoyl)-piperidinyl]-ethyl]-2-methoxy-4-methylaminosulphamoyl-benzamide or a salt thereof, N-[2-[4-(p-fluorobenzoyl)-piperidinyl]-ethyl]-2-methoxy-5-dimethylsulphamoyl-benzamide or a salt thereof, 3-bromo-N-[2-[4-(p-fluorobenzoyl)-piperidinyl]-ethyl]-4-methoxy-benzamide or a salt thereof, N-[2-[4-(p-fluorobenzoyl)-piperidinyl]-ethyl]-2-methoxy-benzamide or a salt thereof, 5-cyano-N-[2-[4-[(4-fluorophenyl)-hydroxymethylene]-piperidinyl]-ethyl]-2-methoxy-benzamide or a salt thereof.

14. A compound according to claim 1 of the formula I being 3-bromo-4-fluoro-N-[2-[4-(p-fluorobenzoyl)-piperidinyl]-ethyl]-benzamide or a salt thereof, 2-bromo-4-fluoro-N-[2-[4-(p-fluorobenzoyl)-piperidinyl]-ethyl]-benzamide or a salt thereof, N-[2-[4-(p-fluorobenzoyl)-piperidinyl]-ethyl]-2,6-dimethoxy-benzamide or a salt thereof, 4-fluoro-N-[2-[4-(p-fluorobenzoyl)-piperidinyl]-ethyl]-benzamide or a salt thereof, 5-bromo-N-[2-[4-(p-fluorobenzoyl)-piperidinyl]-ethyl]-2-methoxy-benzamide or a salt thereof, 3-cyano-N-[2-[4-(p-fluorobenzoyl)-piperidinyl]-ethyl]-4-methoxy-benzamide or a salt thereof.

15. A compound according to claim 1 of the formula I being 3,5-dichloro-N-[2-[4-(p-fluorobenzoyl)-piperidinyl]-3,5-dichloro-N-[2-[4-(p-fluorobenzoyl)-piperidinyl]-ethyl]-2-methoxy-4-methyl-benzamide or a salt thereof, N-[2-[4-(p-fluorobenzoyl)-piperidinyl]-ethyl]-2-methoxy-5-methylmercapto-benzamide or a salt thereof, N-[2-[4-(p-fluorobenzoyl)-piperidinyl]-ethyl]-2-methoxy-5-methanesulphonyl-benzamide or a salt thereof, 5-cyano-N-[2-[4-(p-fluorobenzoyl)-piperidinyl]-ethyl]-2-methoxy-benzamide or a salt thereof, N-[2-[4-(p-fluorobenzoyl)-piperidinyl]-ethyl]-2-methoxy-5-methoxycarbonyl-benzamide or a salt thereof, 5-carbamoyl-N-[2-[4-(p-fluorobenzoyl)-piperidinyl]-ethyl]-2-methoxy-benzamide or a salt thereof, N-[2-[4-(p-fluorobenzoyl)-piperidinyl]-ethyl]-2-methoxy-5-methanesulphinyl-benzamide or a salt thereof, 5-cyano-2-methoxy-N-[2-[4-(2-thenoyl)-piperidinyl]-ethyl]-benzamide or a salt thereof, p-fluoro-N-[2-[4-(2-thenoyl)-piperidinyl]-ethyl]-benzamide or a salt thereof, N-[2-[4-(p-chlorobenzoyl)-piperidinyl]-ethyl]-5-cyano-2-methoxy-benzamide or a salt therof, N-[2-[4-(p-chlorobenzoyl)-piperidinyl]-ethyl]-p-fluoro-benzamide or a salt thereof, p-fluoro-N-[3-[4-(p-fluorobenzoyl)-piperidinyl]-2-methylpropyl]-benzamide or a salt thereof, 5-cyano-N-[3-[4-(p-fluorobenzoyl)-piperidinyl]-propyl]-2-methoxy-benzamide or a salt thereof.

16. A method for treating psychotic diseases in warm-blooded animals comprising treating warm-blooded animals in need of such treatment with an effective amount of a compound of the formula

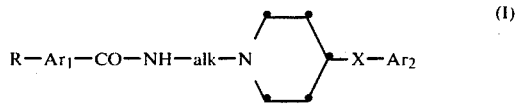

(I)

in which
R represents hydroxy, hydroxy etherified by an aliphatic alcohol, or halogen,
$Ar_1$ represents a monocyclic arylene or heteroarylene radical,
alk represents an alkylene group that separates the two N atoms by at least two carbon atoms,
X represents a free or ketalised carbonyl group, free hydroxymethylene or hydroxymethylene esterified by an organic carboxylic acid, or methylene, and
$Ar_2$ represents a monocyclic aryl or heteroaryl radical,
or a pharmaceutically acceptable salt thereof.

17. A pharmaceutical composition comprising an antipsychotically effective amount of a compound of the formula

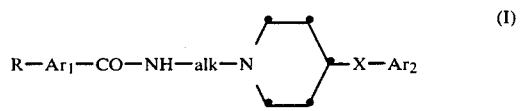

(I)

in which
R represents hydroxy, hydroxy etherified by an aliphatic alcohol, or halogen,
$Ar_1$ represents a monocyclic arylene or heteroarylene radical,
alk represents an alkylene group that separates the two N atoms by at least two carbon atoms,
X represents a free or ketalised carbonyl group, free hydroxymethylene or hydroxymethylene esterified by an organic carboxylic acid, or methylene, and
$Ar_2$ represents a monocyclic aryl or heteroaryl radical,
or a pharmaceutically acceptable salt thereof together with a pharmaceutical carrier.

* * * * *